Figure 1:
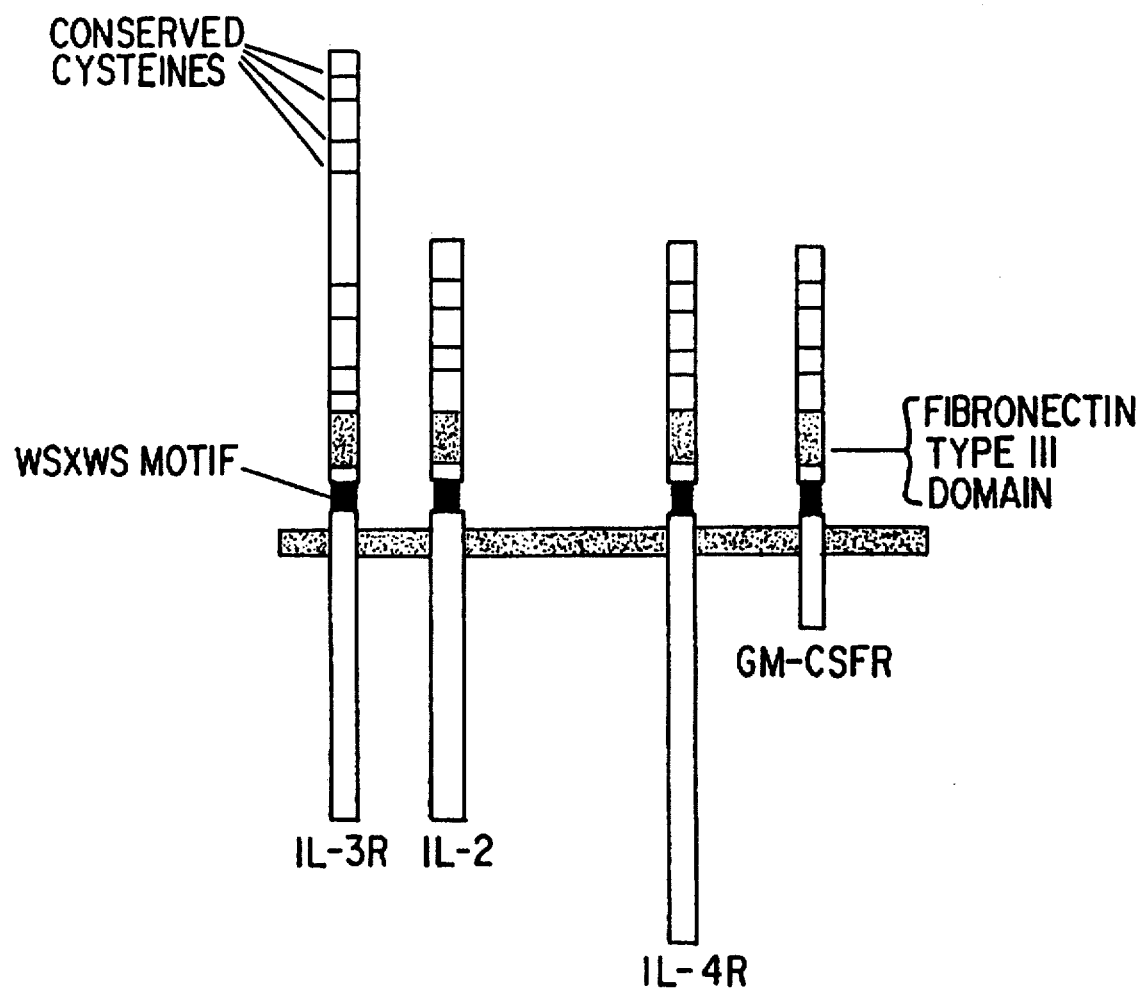

United States Patent [19]

Snodgrass et al.

[11] Patent Number: 5,763,211
[45] Date of Patent: Jun. 9, 1998

[54] ISOLATED NUCLEIC ACID ENCODING HU-B1.219, A NOVEL HUMAN HEMATOPOIETIN

[75] Inventors: H. Ralph Snodgrass, Powell; Joseph Cioffi, Athens; Thomas Joel Zupancic, Worthington; Alan Wayne Shafer, Albany, all of Ohio

[73] Assignee: Progenitor, Inc., Columbus, Ohio

[21] Appl. No.: 355,888

[22] Filed: Dec. 14, 1994

Related U.S. Application Data

[63] Continuation-in-part of Ser. No. 306,231, Sep. 14, 1994, Pat. No. 5,643,748.
[51] Int. Cl.$^6$ .............................. C12N 15/12; C12N 15/62
[52] U.S. Cl. ................... 435/69.1; 435/67.7; 435/252.3; 435/338.1; 536/23.4; 536/23.5
[58] Field of Search ................... 435/69.1, 69.7, 435/252.3, 320.1; 536/23.4, 23.5

[56] References Cited

FOREIGN PATENT DOCUMENTS

| 0 409 607 | 7/1989 | European Pat. Off. . |
| 0 521 156 | 1/1993 | European Pat. Off. . |
| WO 88/02757 | 4/1988 | WIPO . |
| WO 93/10151 | 5/1993 | WIPO . |
| WO 96/07737 | 3/1996 | WIPO . |

OTHER PUBLICATIONS

Jacobs et al, *Nature*, 313:806–810, 28 Feb. 1983.
Sead et al., *P.N.A.S.* 84:3365–3369, May 1987.
Wong et al, *Science* 228:810–815, 17 May 1985.
Miyajima et al., "Receptors For Granulocyte–Macrophage Colony–Stimulating Factor, Interleukin–3, and Interleukin–5", *Blood* 82(7):1960–1974 (1993).
Miyajima et al., "Cytokine Receptors and Signal Transduction", *Annu. Rev. Immunol.* 19:295–331 (1992).
Park et al., "Cloning Of The Low–Affinity Murine Granulocyte–Macrophage Colony–Stimulating Factor Receptor And Reconstitution Of A High–Affinity Receptor Complex", *PNAS U.S.A.* 89:4295–4299 (1992).
Saito et al., "Molecular Cloning Of A Murine IL–6 Receptor–Associated Signal Transducer, gp130, And Its Regulated Expression In Vivo", *J. Immunol.* 148:4066–4071 (1992).
Bazan, "Structural Design And Molecular Evolution Of A Cytokine Receptor Superfamily", *PNAS U.S.A.* 87:6934–6938 (1990).
Cosman et al., "A New Cytokine Receptor Superfamily", *TIBS* pp. 265–269 (Jul. 1990).
Fukunaga et al., "Expression Cloning Of A Receptor For Murine Granulocyte Colony Stimulating Factor", *Cell* 61:341–350 (1990).
Gorman et al., "Cloning and Expression Of A Gene Encoding An Interleukin 3 Receptor–Like Protein: Identification Of Another Member Of The Cytokine Receptor Gene Family", *PNAS U.S.A.* 87:5459–5463 (1990).
Harada et al., "Expression Cloning Of A cDNA Encoding The Murine Interleukin 4 Receptor Based On Ligand Binding", *PNAS U.S.A.* 87:857–861 (1990).
Hayashida et al., "Molecular Cloning Of A Second Subunit Of The Receptor For Human Granulocyte–Macrophage Colony–Stimulating Factor (GM–CSF): Reconstitution Of A High Affinity GM–CSF Receptor", *PNAS U.S.A.* 87:9655–9659 (1990).
Hibi et al., "Molecular Cloning And Expression Of An IL–6 Signal Transducer, gp 130", *Cell* 63:1149–1157 (1990).
Larsen et al., "Expression Cloning Of A Human Granulocyte Colony–Stimulating Factor Receptor: A Structural Mosaic Of Hematopoietin Receptor, Immunoglobulin, And Fibronectin Domains", *J. Exp. Med.* 172:1559–1570 (1990).
Gearing et al., "Expressioin Cloning Of A Receptor For Human Granulocyte–Macrophage Colony–Stimulating Factor", *EMBO J.* 8:3667–7676 (1989).
Mosely et al., "The Murine Interleukin–4 Receptor: Molecular Cloning And Characterization Of Secreted And Membrane Bound Forms", *Cell* 59:335–348 (1989).
Yamasaki et al., "Cloning and Expression Of The Human Interleukin–6 (BSF2/IFNβ2) Receptor", *Science* 241:825–828 (1988).
Gearing et al., "Molecular Cloning And Expression of cDNA Encoding A Murine Myeloid Leukaemia Inhibitory Factor (LIF)", *EMBO J.* 6:3995–4002 (1987).
Ono et al., "A Novel Human Nonviral Retroposon Derived From An Endogenous Retrovirus", *Nuc. Acid. Res.* 15:87250–8737 (1987).
Singer, "Sines and Lines: Highly Repeated Short and Long Interspersed Sequences in Mammalian Genomes", *Cell* 28:433–434 (1982).
Streamson et al., 1996, "Phenotypes of Mouse diabetes and Rat fatty Due to Mutations in the OB (Leptin) Receptor," *Science* 271:994–996.
Cioffi et al., 1996, "Novel B219/OB Receptor Isoforms: Possible Roles of Leptin in Hematopoiesis and Reproduction," *Nature Medicine* 2(5):585–589.
Beckmann et al., 1994, "Molecular Characterization of a Family of Ligands for eph–Related Tyrosine Kinase Receptors," *EMBO Journal* 13(16):3757–3762.
Tartaglia et al., 1995, "Identification and Expression Cloning of a Leptin Receptor, OB–R," *Cell* 83:1263–1271.
Dusanter–Fourt et al., 1994, "Transduction du Signal Par Les Recepteurs De Cytokines," *Medecine Sciences* 10:825–835.
Truett et al., 1991, "Rat Obesity Gene fatty (fa) Mapps to Chromosome 5: Evidence for Homology with the Mouse Gene diabetes (db)," *Proc. Natl. Acad. Sci. U.S.A.* 88:7806–7809.
Bahary et al., 1990, "Molecular Mapping of the Mouse db Mutation," *Proc. Natl. Acad. Sci. U.S.A.*, 87:8642–8646.

*Primary Examiner*—John Ulm
*Attorney, Agent, or Firm*—Pennie & Edmonds LLP

[57] ABSTRACT

The present invention relates to a novel member of the hematopoietin receptor family; herein referred to as Hu-B1.219. In particular, the invention relates to nucleotide sequences and expression vectors encoding Hu-B1.219 gene product Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

54 Claims, 11 Drawing Sheets

```
              9           18          27          36          45          54
GCG CGC GCG ACG CAG GTG CCC GAG CCC CGG CCC GCG CCC ATC TCT GCC TTC GGT
--- --- --- --- --- --- --- --- --- --- --- --- --- --- --- --- --- ---
 A   R   A   T   Q   V   P   E   P   R   P   A   P   I   S   A   F   G 63          72          81          90          99         108
CGA GTT GGA CCC CCG GAT CAA GGT GTA CTT CTC TGA AGT AAG ATG ATT TGT CAA
--- --- --- --- --- --- --- --- --- --- --- --- --- --- --- --- --- ---
 R   V   G   P   P   D   Q   G   V   L   L   *   S   K   M   I   C   Q 117         126         135         144         153         162
AAA TTC TGT GTG GTT TTG TTA CAT TGG GAA TTT ATT TAT GTG ATA ACT GCG TTT
--- --- --- --- --- --- --- --- --- --- --- --- --- --- --- --- --- ---
 K   F   C   V   V   L   L   H   W   E   F   I   Y   V   I   T   A   F 171         180         189         198         207         216
AAC TTG TCA TAT CCA ATT ACT CCT TGG AGA TTT AAG TTG TCT TGC ATG CCA CCA
--- --- --- --- --- --- --- --- --- --- --- --- --- --- --- --- --- ---
 N   L   S   Y   P   I   T   P   W   R   F   K   L   S   C   M   P   P 225         234         243         252         261         270
AAT TCA ACC TAT GAC TAC TTC CTT TTG CCT GCT GGA CTC TCA AAG AAT ACT TCA
--- --- --- --- --- --- --- --- --- --- --- --- --- --- --- --- --- ---
 N   S   T   Y   D   Y   F   L   L   P   A   G   L   S   K   N   T   S 279         288         297         306         315         324
AAT TCG AAT GGA CAT TAT GAG ACA GCT GTT GAA CCT AAG TTT AAT TCA AGT GGT
--- --- --- --- --- --- --- --- --- --- --- --- --- --- --- --- --- ---
 N   S   N   G   H   Y   E   T   A   V   E   P   K   F   N   S   S   G 333         342         351         360         369         378
ACT CAC TTT TCT AAC TTA TCC AAA GCA ACT TTC CAC TGT TGC TTT CGG AGT GAG
--- --- --- --- --- --- --- --- --- --- --- --- --- --- --- --- --- ---
 T   H   F   S   N   L   S   K   A   T   F   H   C   C   F   R   S   E 387         396         405         414         423         432
CAA GAT AGA AAC TGC TCC TTA TGT GCA GAC AAC ATT GAA GGA AGG ACA TTT GTT
--- --- --- --- --- --- --- --- --- --- --- --- --- --- --- --- --- ---
 Q   D   R   N   C   S   L   C   A   D   N   I   E   G   R   T   F   V
```

FIG.2A

```
        441         450         459         468         477         486
TCA ACA GTA AAT TCT TTA GTT TTT CAA CAA ATA GAT GCA AAC TGG AAC ATA CAG
--- --- --- --- --- --- --- --- --- --- --- --- --- --- --- --- --- ---
 S   T   V   N   S   L   V   F   Q   Q   I   D   A   N   W   N   I   Q 495         504         513         522         531         540
TGC TGG CTA AAA GGA GAC TTA AAA TTA TTC ATC TGT TAT GTG GAG TCA TTA TTT
--- --- --- --- --- --- --- --- --- --- --- --- --- --- --- --- --- ---
 C   W   L   K   G   D   L   K   L   F   I   C   Y   V   E   S   L   F 549         558         567         576         585         594
AAG AAT CTA TTC AGG AAT TAT AAC TAT AAG GTC CAT CTT TTA TAT GTT CTG CCT
--- --- --- --- --- --- --- --- --- --- --- --- --- --- --- --- --- ---
 K   N   L   F   R   N   Y   N   Y   K   V   H   L   L   Y   V   L   P 603         612         621         630         639         648
GAA GTG TTA GAA GAT TCA CCT CTG GTT CCC CAA AAA GGC AGT TTT CAG ATG GTT
--- --- --- --- --- --- --- --- --- --- --- --- --- --- --- --- --- ---
 E   V   L   E   D   S   P   L   V   P   Q   K   G   S   F   Q   M   V 657         666         675         684         693         702
CAC TGC AAT TGC AGT GTT CAT GAA TGT TGT GAA TGT CTT GTG CCT GTG CCA ACA
--- --- --- --- --- --- --- --- --- --- --- --- --- --- --- --- --- ---
 H   C   N   C   S   V   H   E   C   C   E   C   L   V   P   V   P   T 711         720         729         738         747         756
GCC AAA CTC AAC GAC ACT CTC CTT ATG TGT TTG AAA ATC ACA TCT GGT GGA GTA
--- --- --- --- --- --- --- --- --- --- --- --- --- --- --- --- --- ---
 A   K   L   N   D   T   L   L   M   C   L   K   I   T   S   G   G   V 765         774         783         792         801         810
ATT TTC CGG TCA CCT CTA ATG TCA GTT CAG CCC ATA AAT ATG GTG AAG CCT GAT
--- --- --- --- --- --- --- --- --- --- --- --- --- --- --- --- --- ---
 I   F   R   S   P   L   M   S   V   Q   P   I   N   M   V   K   P   D 819         828         837         846         855         864
CCA CCA TTA GGT TTG CAT ATG GAA ATC ACA GAT GAT GGT AAT TTA AAG ATT TCT
--- --- --- --- --- --- --- --- --- --- --- --- --- --- --- --- --- ---
 P   P   L   G   L   H   M   E   I   T   D   D   G   N   L   K   I   S
```

FIG.2B

```
      873           882           891           900           909           918
TGG TCC AGC CCA CCA TTG GTA CCA TTT CCA CTT CAA TAT CAA GTG AAA TAT TCA
--- --- --- --- --- --- --- --- --- --- --- --- --- --- --- --- --- ---
 W   S   S   P   P   L   V   P   F   P   L   Q   Y   Q   V   K   Y   S 927           936           945           954           963           972
GAG AAT TCT ACA ACA GTT ATC AGA GAA GCT GAC AAG ATT GTC TCA GCT ACA TCC
--- --- --- --- --- --- --- --- --- --- --- --- --- --- --- --- --- ---
 E   N   S   T   T   V   I   R   E   A   D   K   I   V   S   A   T   S 981           990           999          1008          1017          1026
CTG CTA GTA GAC AGT ATA CTT CCT GGG TCT TCG TAT GAG GTT CAG GTG AGG GGC
--- --- --- --- --- --- --- --- --- --- --- --- --- --- --- --- --- ---
 L   L   V   D   S   I   L   P   G   S   S   Y   E   V   Q   V   R   G 1035          1044          1053          1062          1071          1080
AAG AGA CTG GAT GGC CCA GGA ATC TGG AGT GAC TGG AGT ACT CCT CGT GTC TTT
--- --- --- --- --- --- --- --- --- --- --- --- --- --- --- --- --- ---
 K   R   L   D   G   P   G   I   W   S   D   W   S   T   P   R   V   F 1089          1098          1107          1116          1125          1134
ACC ACA CAA GAT GTC ATA TAC TTT CCA CCT AAA ATT CTG ACA AGT GTT GGG TCT
--- --- --- --- --- --- --- --- --- --- --- --- --- --- --- --- --- ---
 T   T   Q   D   V   I   Y   F   P   P   K   I   L   T   S   V   G   S 1143          1152          1161          1170          1179          1188
AAT GTT TCT TTT CAC TGC ATC TAT AAG AAG GAA AAC AAG ATT GTT CCC TCA AAA
--- --- --- --- --- --- --- --- --- --- --- --- --- --- --- --- --- ---
 N   V   S   F   H   C   I   Y   K   K   E   N   K   I   V   P   S   K 1197          1206          1215          1224          1233          1242
GAG ATT GTT TGG TGG ATG AAT TTA GCT GAG AAA ATT CCT CAA AGC CAG TAT GAT
--- --- --- --- --- --- --- --- --- --- --- --- --- --- --- --- --- ---
 E   I   V   W   W   M   N   L   A   E   K   I   P   Q   S   Q   Y   D 1251          1260          1269          1278          1287          1296
GTT GTG AGT GAT CAT GTT AGC AAA GTT ACT TTT TTC AAT CTG AAT GAA ACC AAA
--- --- --- --- --- --- --- --- --- --- --- --- --- --- --- --- --- ---
 V   V   S   D   H   V   S   K   V   T   F   F   N   L   N   E   T   K
```

FIG.2C

```
      1305            1314            1323            1332            1341            1350
CCT CGA GGA AAG TTT ACC TAT GAT GCA GTG TAC TGC TGC AAT GAA CAT GAA TGC
--- --- --- --- --- --- --- --- --- --- --- --- --- --- --- --- --- ---
 P   R   G   K   F   T   Y   D   A   V   Y   C   C   N   E   H   E   C 1359            1368            1377            1386            1395            1404
CAT CAT CGC TAT GCT GAA TTA TAT GTG ATT GAT GTC AAT ATC AAT ATC TCA TGT
--- --- --- --- --- --- --- --- --- --- --- --- --- --- --- --- --- ---
 H   H   R   Y   A   E   L   Y   V   I   D   V   N   I   N   I   S   C 1413            1422            1431            1440            1449            1458
GAA ACT GAT GGG TAC TTA ACT AAA ATG ACT TGC AGA TGG TCA ACC AGT ACA ATC
--- --- --- --- --- --- --- --- --- --- --- --- --- --- --- --- --- ---
 E   T   D   G   Y   L   T   K   M   T   C   R   W   S   T   S   T   I 1467            1476            1485            1494            1503            1512
CAG TCA CTT GCG GAA AGC ACT TTG CAA TTG AGG TAT CAT AGG AGC AGC CTT TAC
--- --- --- --- --- --- --- --- --- --- --- --- --- --- --- --- --- ---
 Q   S   L   A   E   S   T   L   Q   L   R   Y   H   R   S   S   L   Y 1521            1530            1539            1548            1557            1566
TGT TCT GAT ATT CCA TCT ATT CAT CCC ATA TCT GAG CCC AAA GAT TGC TAT TTG
--- --- --- --- --- --- --- --- --- --- --- --- --- --- --- --- --- ---
 C   S   D   I   P   S   I   H   P   I   S   E   P   K   D   C   Y   L 1575            1584            1593            1602            1611            1620
CAG AGT GAT GGT TTT TAT GAA TGC ATT TTC CAG CCA ATC TTC CTA TTA TCT GGC
--- --- --- --- --- --- --- --- --- --- --- --- --- --- --- --- --- ---
 Q   S   D   G   F   Y   E   C   I   F   Q   P   I   F   L   L   S   G 1629            1638            1647            1656            1665            1674
TAC ACA ATG TGG ATT AGG ATC AAT CAC TCT CTA GGT TCA CTT GAC TCT CCA CCA
--- --- --- --- --- --- --- --- --- --- --- --- --- --- --- --- --- ---
 Y   T   M   W   I   R   I   N   H   S   L   G   S   L   D   S   P   P
```

FIG. 2D

```
         1683          1692          1701          1710          1719          1728
ACA TGT GTC CTT CCT GAT TCT GTG GTG AAG CCA CTG CCT CCA TCC AGT GTG AAA
--- --- --- --- --- --- --- --- --- --- --- --- --- --- --- --- --- ---
 T   C   V   L   P   D   S   V   V   K   P   L   P   P   S   S   V   K 1737          1746          1755          1764          1773          1782
GCA GAA ATT ACT ATA AAC ATT GGA TTA TTG AAA ATA TCT TGG GAA AAG CCA GTC
--- --- --- --- --- --- --- --- --- --- --- --- --- --- --- --- --- ---
 A   E   I   T   I   N   I   G   L   L   K   I   S   W   E   K   P   V 1791          1800          1809          1818          1827          1836
TTT CCA GAG AAT AAC CTT CAA TTC CAG ATT CGC TAT GGT TTA AGT GGA AAA GAA
--- --- --- --- --- --- --- --- --- --- --- --- --- --- --- --- --- ---
 F   P   E   N   N   L   Q   F   Q   I   R   Y   G   L   S   G   K   E 1845          1854          1863          1872          1881          1890
GTA CAA TGG AAG ATG TAT GAG GTT TAT GAT GCA AAA TCA AAA TCT GTC AGT CTC
--- --- --- --- --- --- --- --- --- --- --- --- --- --- --- --- --- ---
 V   Q   W   K   M   Y   E   V   Y   D   A   K   S   K   S   V   S   L 1899          1908          1917          1926          1935          1944
CCA GTT CCA GAC TTG TGT GCA GTC TAT GCT GTT CAG GTG CGC TGT AAG AGG CTA
--- --- --- --- --- --- --- --- --- --- --- --- --- --- --- --- --- ---
 P   V   P   D   L   C   A   V   Y   A   V   Q   V   R   C   K   R   L 1953          1962          1971          1980          1989          1998
GAT GGA CTG GGA TAT TGG AGT AAT TGG AGC AAT CCA GCC TAC ACA GTT GTC ATG
--- --- --- --- --- --- --- --- --- --- --- --- --- --- --- --- --- ---
 D   G   L   G   Y   W   S   N   W   S   N   P   A   Y   T   V   V   M 2007          2016          2025          2034          2043          2052
GAT ATA AAA GTT CCT ATG AGA GGA CCT GAA TTT TGG AGA ATA ATT AAT GGA GAT
--- --- --- --- --- --- --- --- --- --- --- --- --- --- --- --- --- ---
 D   I   K   V   P   M   R   G   P   E   F   W   R   I   I   N   G   D 2061          2070          2079          2088          2097          2106
ACT ATG AAA AAG GAG AAA AAT GTC ACT TTA CTT TGG AAG CCC CTG ATG AAA AAT
--- --- --- --- --- --- --- --- --- --- --- --- --- --- --- --- --- ---
 T   M   K   K   E   K   N   V   T   L   L   W   K   P   L   M   K   N
```

FIG.2E

```
        2115            2124            2133            2142            2151            2160
GAC TCA TTG TGC AGT GTT CAG AGA TAT GTG ATA AAC CAT CAT ACT TCC TGC AAT
--- --- --- --- --- --- --- --- --- --- --- --- --- --- --- --- --- ---
 D   S   L   C   S   V   Q   R   Y   V   I   N   H   H   T   S   C   N 2169            2178            2187            2196            2205            2214
GGA ACA TGG TCA GAA GAT GTG GGA AAT CAC ACG AAA TTC ACT TTC CTG TGG ACA
--- --- --- --- --- --- --- --- --- --- --- --- --- --- --- --- --- ---
 G   T   W   S   E   D   V   G   N   H   T   K   F   T   F   L   W   T 2223            2232            2241            2250            2259            2268
GAG CAA GCA CAT ACT GTT ACG GTT CTG GCC ATC AAT TCA ATT GGT GCT TCT GTT
--- --- --- --- --- --- --- --- --- --- --- --- --- --- --- --- --- ---
 E   Q   A   H   T   V   T   V   L   A   I   N   S   I   G   A   S   V 2277            2286            2295            2304            2313            2322
GCA AAT TTT AAT TTA ACC TTT TCA TGG CCT ATG AGC AAA GTA AAT ATC GTG CAG
--- --- --- --- --- --- --- --- --- --- --- --- --- --- --- --- --- ---
 A   N   F   N   L   T   F   S   W   P   M   S   K   V   N   I   V   Q 2331            2340            2349            2358            2367            2376
TCA CTC AGT GCT TAT CCT TTA AAC AGC AGT TGT GTG ATT GTT TCC TGG ATA CTA
--- --- --- --- --- --- --- --- --- --- --- --- --- --- --- --- --- ---
 S   L   S   A   Y   P   L   N   S   S   C   V   I   V   S   W   I   L 2385            2394            2403            2412            2421            2430
TCA CCC AGT GAT TAC AAG CTA ATG TAT TTT ATT ATT GAG TGG AAA AAT CTT AAT
--- --- --- --- --- --- --- --- --- --- --- --- --- --- --- --- --- ---
 S   P   S   D   Y   K   L   M   Y   F   I   I   E   W   K   N   L   N 2439            2448            2457            2466            2475            2484
GAA GAT GGT GAA ATA AAA TGG CTT AGA ATC TCT TCA TCT GTT AAG AAG TAT TAT
--- --- --- --- --- --- --- --- --- --- --- --- --- --- --- --- --- ---
 E   D   G   E   I   K   W   L   R   I   S   S   S   V   K   K   Y   Y 2493            2502            2511            2520            2529            2538
ATC CAT GAT CAT TTT ATC CCC ATT GAG AAG TAC CAG TTC AGT CTT TAC CCA ATA
--- --- --- --- --- --- --- --- --- --- --- --- --- --- --- --- --- ---
 I   H   D   H   F   I   P   I   E   K   Y   Q   F   S   L   Y   P   I
```

FIG.2F

```
     2547         2556         2565         2574         2583         2592
TTT ATG GAA GGA GTG GGA AAA CCA AAG ATA ATT AAT AGT TTC ACT CAA GAT GAT
--- --- --- --- --- --- --- --- --- --- --- --- --- --- --- --- --- ---
 F   M   E   G   V   G   K   P   K   I   I   N   S   F   T   Q   D   D 2601         2610         2619         2628         2637         2646
ATT GAA AAA CAC CAG AGT GAT GCA GGT TTA TAT GTA ATT GTG CCA GTA ATT ATT
--- --- --- --- --- --- --- --- --- --- --- --- --- --- --- --- --- ---
 I   E   K   H   Q   S   D   A   G   L   Y   V   I   V   P   V   I   I 2655         2664         2673         2682         2691         2700
TCC TCT TCC ATC TTA TTG CTT GGA ACA TTA TTA ATA TCA CAC CAA AGA ATG AAA
--- --- --- --- --- --- --- --- --- --- --- --- --- --- --- --- --- ---
 S   S   S   I   L   L   L   G   T   L   L   I   S   H   Q   R   M   K 2709         2718         2727         2736         2745         2754
AAG CTA TTT TGG GAA GAT GTT CCG AAC CCC AAG AAT TGT TCC TGG GCA CAA GGA
--- --- --- --- --- --- --- --- --- --- --- --- --- --- --- --- --- ---
 K   L   F   W   E   D   V   P   N   P   K   N   C   S   W   A   Q   G 2763         2772         2781         2790         2799         2808
CTT AAT TTT CAG AAG ATG CTT GAA GGC AGC ATG TTC GTT AAG AGT CAT CAC CAC
--- --- --- --- --- --- --- --- --- --- --- --- --- --- --- --- --- ---
 L   N   F   Q   K   M   L   E   G   S   M   F   V   K   S   H   H   H 2817         2826         2835         2844         2853         2862
TCC CTA ATC TCA AGT ACC CAG GGA CAC AAA CAC TGC GGA AGG CCA CAG GGT CCT
--- --- --- --- --- --- --- --- --- --- --- --- --- --- --- --- --- ---
 S   L   I   S   S   T   Q   G   H   K   H   C   G   R   P   Q   G   P 2871
     2880         2889         2898         2907         2916
CTG CAT AGG AAA ACC AGA GAC CTT TGT TCA CTT GTT TAT CTG CTG ACC CTC CCT
--- --- --- --- --- --- --- --- --- --- --- --- --- --- --- --- --- ---
 L   H   R   K   T   R   D   L   C   S   L   V   Y   L   L   T   L   P 2925         2934         2943         2952         2961         2970
CCA CTA TTG TCC TAT GAC CCT GCC AAA TCC CCC TCT GTG AGA AAC ACC CAA GAA
--- --- --- --- --- --- --- --- --- --- --- --- --- --- --- --- --- ---
 P   L   L   S   Y   D   P   A   K   S   P   S   V   R   N   T   Q   E 2979         2988
TGA TCA ATA AAA AAA AAA AAA 3'
--- --- --- --- --- --- ---
 *   S   I   K   K   K   K
```

FIG.2G

|  |  |  | 2760 | 2770 | 2780 | 2790 | 2800 |  |
|---|---|---|---|---|---|---|---|---|
| HuB1.219 Form | 1 | 2751 | AGGACTTAAT | TTTCAGAAGA | TGCTTGAAGG | CAGCATGTTC | GTTAAGAGTC | 2800 |
| HuB1.219 | 2 | 2751 | AGGACTTAAT | TTTCAGAAGA | AAATGCCTGG | CACAAAGGAA | CTACTGGGTG | 2800 |
| HuB1.219 | 3 | 2751 | AGGACTTAAT | TTTCAGAAGA | GAACGGACAT | TCTTTGAAGT | CTAATCATGA | 2800 |
|  |  |  | 2810 | 2820 | 2830 | 2840 | 2850 |  |
| HuB1.219 Form | 1 | 2801 | ATCACCACTC | CCTAATCTCA | AGTACCCAGG | GACACAAACA | CTGCGGAAGG | 2850 |
| HuB1.219 | 2 | 2801 | GAGGTTGGTT | GACTTAGGAA | ATGCTTGTGA | AGCTACGTCC | TACCTCGTGC | 2850 |
| HuB1.219 | 3 | 2801 | TCACTACAGA | TGAACCCAAT | GTGCCAACTT | CCCAACAGTC | TATAGAGTAT | 2850 |
|  |  |  | 2860 | 2870 | 2880 | 2890 | 2900 |  |
| HuB1.219 Form | 1 | 2851 | CCACAGGGTC | CTCTGCATAG | GAAAACCAGA | GACCTTTGTT | CACTTGTTTA | 2900 |
| HuB1.219 | 2 | 2851 | GCACCTGCTC | TCCCTGAGGT | GTGCACAATG | .......... | .......... | 2900 |
| HuB1.219 | 3 | 2851 | TAGAAGATTT | TTACATTCTG | AAGAAGG... | .......... | .......... | 2900 |
|  |  |  | 2910 | 2920 | 2930 | 2940 | 2950 |  |
| HuB1.219 Form | 1 | 2901 | TCTGCTGACC | CTCCCTCCAC | TATTGTCCTA | TGACCCTGCC | AAATCCCCCT | 2950 |
| HuB1.219 | 2 | 2901 | .......... | .......... | .......... | .......... | .......... | 2950 |
| HuB1.219 | 3 | 2901 | .......... | .......... | .......... | .......... | .......... | 2950 |
|  |  |  | 2960 | 2970 | 2980 | 2990 | 3000 |  |
| HuB1.219 Form | 1 | 2951 | CTGTGAGAAA | CACCCAAGAA | TGATCAATAA | AAAAAAAAAA | A......... | 3000 |
| HuB1.219 | 2 | 2951 | .......... | .......... | .......... | .......... | .......... | 3000 |
| HuB1.219 | 3 | 2951 | .......... | .......... | .......... | .......... | .......... | 3000 |

FIG.3A

|  |  |  | 10 | 20 | 30 | 40 | 50 |  |
|---|---|---|---|---|---|---|---|---|
| HuB1.219 Form | 1 | 1 | GLNFQKMLEG | SMFVKSHHHS | LISSTQGHKH | CGRPQGPLHR | KTRDLCSLVY | 50 |
| HuB1.219 | 2 | 1 | GLNFQKKMPG | TKELLGGGWL | T*EMLVKLRP | TSCAPALPEV | CTM....... | 50 |
| HuB1.219 | 3 | 1 | GLNFQKRTDI | L*SLIMITTD | EPNVPTSQQS | IEY*KIFTF* | RR........ | 50 |
|  |  |  | 60 | 70 | 80 | 90 | 100 |  |
| HuB1.219 Form | 1 | 51 | LLTLPPLLSY | DPAKSPSVRN | TQE*SIKKKK | .......... | .......... | 100 |
| HuB1.219 | 2 | 51 | .......... | .......... | .......... | .......... | .......... | 100 |
| HuB1.219 | 3 | 51 | .......... | .......... | .......... | .......... | .......... | 100 |

FIG.3B

SPACING OF CONSERVED AMINO ACIDS IN THE EXTRACELLULAR
DOMAINS OF KNOWN CYTOKINE RECEPTOR GENES

..C...C..........C..........A/PP.L/V.....W......Y.............L..Y..R....G..WSXWS..
(10-11) (28-35)    (9-16)        (36-48)        (2-3) (13-18) (12-20)    (26-33)  (5-6)(5)(6-11)(2)

CONSERVED AMINO ACIDS IN THE 5' EXTRACELLULAR DOMAINS OF CLONE Hu-B1.219

..C...C..........C..........PP.L.....W......Y.............L..Y..R....G..WSDWS..
(11)  (44)          (10)         (43)    (3)   (14)    (12)          (30)    (5)  (5)(8)(2)

CONSERVED AMINO ACIDS IN THE 3' EXTRACELLULAR DOMAINS OF CLONE Hu-B1.219

..C...C..........C..........PP.V.....W......Y.............P..Y..R....G..WSNWS..
(11)  (41)          (10)         (41)    (3)   (15)    (16)          (27)    (6)  (5)(8)(2)

FIG.4

```
                         * _ * _ * _
mIL2Rβ           E P Y L E F E A R R R L L
hIL2Rγ           E H L V Q Y R T D W D H S
mIL5Rα           D H C F N Y E L K I Y N T
mEPOR            T T H I R Y E V D V S A G
Hu-B1.219(5')    P F P L Q Y Q V K Y Q V K
Hu-B1.219(3')    Q F Q I R Y G L S G K E V

HYDROPHOBIC:  "*"
HYDROPHILIC:  "-"
```

FIG.5

```
                         * b * b * b
mIL-2Rβ          S T S Y E V Q V R V K A Q R N
hIL-2Rγ          Q K R Y T F R V R S R F N P L
mIL-5Rα          L S K Y D V Q V R A A V S S M
mEPOR            G T R Y T F A V R A R M A P S
Hu-B1.219(5')    G S S Y E V Q V R G K R L D G
Hu-B1.219(3')    C A V Y A V Q V R C K R L D G
                         Y         R

HYDROPHOBIC:  "*"
BASIC:        "b"
```

FIG.6

ISOLATED NUCLEIC ACID ENCODING HU-B1.219, A NOVEL HUMAN HEMATOPOIETIN

The present application is a continuation-in-part of U.S. patent application Ser. No. 08/306,231, filed Sep. 14, 1994, U.S. Pat No. 5,643,748 which is incorporated by reference herein in its entirety.

1. INTRODUCTION

The present invention relates to a novel member of the hematopoietin receptor family, herein referred to as Hu-B1.219. In particular, the invention relates to nucleotide sequences and expression vectors encoding Hu-B1.219 gene product. Genetically engineered host cells that express the Hu-B1.219 coding sequence may be used to evaluate and screen for ligands or drugs involved in Hu-B1.219 interaction and regulation. Since Hu-B1.219 expression has been detected in certain human fetal tissues and cancer cells, molecular probes designed from its nucleotide sequence may be useful for prenatal testing and cancer diagnosis.

2. BACKGROUND OF THE INVENTION

A variety of diseases, including malignancy and immunodeficiency, are related to malfunction within the lympho-hematopoietic system. Some of these conditions could be alleviated and/or cured by repopulating the hematopoietic system with progenitor cells, which when triggered to differentiate would overcome the patient's deficiency. Therefore, the ability to initiate and regulate hematopoiesis is of great importance (McCune et al., 1988, Science 241:1632).

The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors or cytokines (Metcalf, 1985, Science 229:16; Dexter, 1987, J. Cell Sci. 88:1; Golde and Gasson, 1988, Scientific American, July:62; Tabbara and Robinson, 1991, Anti-Cancer Res. 11:81; Ogawa, 1989, Environ. Health Presp. 80:199; Dexter, 1989, Br. Med. Bull. 45:337).

With the advent of recombinant DNA technology, the genes encoding a number of these molecules have now been molecularly cloned and expressed in recombinant form (Souza et al., 1986, Science 232:61; Gough et al., 1984, Nature 5 309:763; Yokota et al., 1984, Proc. Natl. Acad. Sci. U.S.A. 81:1070; Kawasaki et al., 1985, Science 230:291). These cytokines have been studied in their structure, biology and even therapeutic potential. Some of the most well characterized factors include erythropoietin (EPO), stem cell factor (SCF), granulocyte macrophage colony stimulating factor (GM-CSF), macrophage colony stimulating factor (M-CSF), granulocyte colony stimulating factor (G-CSF), and the interleukins (IL-1 to IL-14).

These factors act on different cell types at different stages during blood cell development, and their potential uses in medicine are far-reaching which include blood transfusions, bone marrow transplantation, correcting immunosuppressive disorders, cancer therapy, wound healing, and activation of the immune response. (Golde and Gasson, 1988, Scientific American, July:62).

Apart from inducing proliferation and differentiation of hesmatopoietic progenitor cells, such cytokines have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

Cytokines exert their effects on target cells by binding to specific cell surface receptors. A number of cytokine receptors have been identified and the genes encoding them molecularly cloned. Several cytokine receptors have recently been classified into a hematopoietin receptor (HR) superfamily. The grouping of these receptors was based on the conservation of key amino acid motifs in the extracellular domains (Bazan, 1990, Immunology Today 11:350) (FIG. 1). The HR family is defined by three conserved motifs in the extracellular domain of these receptors. The first is a Trp-Ser-X-Trp-Ser (WSXWS box) motif (SEQ ID No. 1) which is highly conserved and located amino-terminal to the transmembrane domain. Most members of the HR family contain this motif. The second consists of four conserved cysteine residues located in the amino-terminal half of the extracellular region. The third is a conserved fibronectin Type III (FN III) domain which is located between the WSXWS box and the cysteines. The members of the HR family include receptors for ligands such as erythropoietin (EPO), granulocyte colony stimulating factor (G-CSF) (Fukunaga, 1990, Cell 61:341), granulocyte-macrophage colony stimulating factor (GM-CSF), interleukin-3 (IL-3), IL-4, IL-5, IL-6, IL-7, and IL-2 (β-subunit) (Cosman, 1990, TIBS 15:265).

Ligands for the HR are critically involved in the maturation and differentiation of blood cells. For example, IL-3 promotes the proliferation of early multilineage pluripotent stem cells, and synergizes with EPO to produce red cells. IL-6 and IL-3 synergize to induce proliferation of early hematopoietic precursors. GM-CSF has been shown to induce the proliferation of granulocytes as well as increase macrophage function. IL-7 is a bone marrow-derived cytokine that plays a role in producing immature T and B lymphocytes. IL-4 induces proliferation of antigen-primed B cells and antigen-specific T cells. Thus, members of this receptor superfamily are involved in the regulation of the hematopoietic system.

3. SUMMARY OF THE INVENTION

The present invention relates to a novel member of the HR family, referred to as Hu-B1.219. In particular, it relates to the nucleotide sequences, expression vectors, host cells expressing the Hu-B1.219 gene, and proteins encoded by the sequences.

The invention is based, in part, upon Applicants' discovery of a cDNA clone, Hu-B1.219, isolated from a human fetal liver cDNA library. While the nucleotide sequence of this clone shares certain homology with other HR genes, it is also unique in its structure. Three forms of Hu-B1.219 have been identified, and they differ in sequence only at their 3' ends. The sequences are expressed in certain human fetal and tumor cells. Therefore, a wide variety of uses are encompassed by the present invention, including but not limited to, the diagnosis of cancer, the marking of fetal tissues, and the screening of ligands and compounds that bind the receptor molecule encoded by Hu-B1.219.

For the purpose of the present invention, the designation Hu-B1.219 refers to the complete cDNA sequence disclosed in FIG. 2A-2G. In addition, Hu-B1.219 also refers to the partial coding sequences within the cDNA sequence of FIG. 2A-2G.

4. BRIEF DESCRIPTION OF THE DRAWINGS

FIG. 1. A schematic drawing of conserved regions shared by members of HR family.

FIG. 2A-2G. Nucleotide sequence (SEQ ID No: 6) and deduced amino acid sequence (SEQ ID No: 7, 8, 9) of Hu-B1.219.

FIG. 3A. Comparison of 3' end nucleotide sequences of the three forms of the Hu-B1.219 Form 1 (SEQ ID No: 8); Form 2 (SEQ ID No: 13); Form 3 (SEQ ID No: 16.

FIG. 3B. Comparison of 3' end amino acid sequences of the three forms of Hu-B1.219 Form 1 (SEQ ID No: 11, 12); Form 2 (SEQ ID No: 14,15); Form 3 (SEQ ID No: 17, 18, 19. The * symbol indicates a stop codon.

FIG. 4. Comparison of the spacing of conserved amino acids in the FN III domain between HR genes and Hu-B1.219.

FIG. 5. Comparison of conserved motifs between HR molecules and Hu-B1.219 in "Block 3" mIL2Rβ (SEQ ID No: 20); hIL2Rγ (SEQ ID No: 21); mIL5Rα (SEQ ID No: 22); mEPOR (SEQ ID No: 23); Hu-B1.219 (5') (SEQ ID No: 30); Hu-B1.219 (3') (SEQ ID No: 31).

FIG. 6. Comparison of conserved motifs between HR molecules and Hu-B1.219 in "Block 6" mIL-2Rβ (SEQ ID No: 26); hIL-2Rγ (SEQ ID No: 21); mIL-5Rα (SEQ ID No: 28); mEPOR (SEQ ID No: 29); Hu-B1.219 (5') (SEQ ID No: 30); Hu-B1.219 (3') (SEQ ID No: 31).

5. DETAILED DESCRIPTION OF THE INVENTION

5.1. The Hu-B1.219 Coding Sequence

The present invention relates to nucleic acid and amino acid sequences of a novel member of the HR family. In a specific embodiment by way of example in Section 6, infra, a new member of this HR family of receptors was cloned and characterized. The nucleotide coding sequence and deduced amino acid sequence of the novel receptor are unique, and the receptor is referred to as Hu-B1.219. In accordance with the invention, any nucleotide sequence which encodes the amino acid sequence of the Hu-B1.219 gene product can be used to generate recombinant molecules which direct the expression of Hu-B1.219 gene.

Analysis of the Hu-B1.219 sequence revealed significant homology to the FN III domain of the HR family indicating that it was a member of the HR family of receptors. The shared homology between Hu-B1.219 and other known members of the HR family is discussed in Section 6.2, infra. However, this receptor also contains regions of previously unreported unique nucleotide sequences.

Northern blot hybridization analysis, indicates that Hu-B1.219 mRNA is highly expressed in cells of hematopoietic origin. In addition, the Hu-B1.219 sequence is expressed in certain tumor cells.

In order to clone the full length cDNA sequence encoding the entire Hu-B1.219 cDNA or to clone variant forms of the molecule, labeled DNA probes made from nucleic acid fragments corresponding to any portion of the partial cDNA disclosed herein may be used to screen the human fetal liver cDNA library. More specifically, oligonucleotides corresponding to either the 5' or 3' terminus of the partial cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon Filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabeled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained. It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cNA Ends) technique may be used. RACE is a proven PCR-based strategy for amplifying the 5' end of incomplete cDNAs. 5' RACE-Ready cDNA synthesized from human fetal liver containing a unique anchor sequence is commercially available (Clontech). To obtain the 5' end of the CDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and transmembrane domain, and finally overall structural similarity to known HR genes.

5.2. Expression of Hu-B1.219 Sequence

In accordance with the invention, Hu-B1.219 polynucleotide sequence which encodes the Hu-B1.219 protein, peptide fragments of Hu-B1.219, Hu-B1.219 fusion proteins or functional equivalents thereof, may be used to generate recombinant DNA molecules that direct the expression of Hu-B1.219 protein, Hu-B1.219 peptide fragment, fusion proteins or a functional equivalent thereof, in appropriate host cells. Such Hu-B1.219 polynucleotide sequences, as well as other polynucleotides which selectively hybridize to at least a part of such Hu-B1.219 polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Hu-B1.219 protein. Such DNA sequences include those which are capable of hybridizing to the human Hu-B1.219 sequences under stringent conditions. The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) Formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Hu-B1.219 sequence, which result in a silent change thus producing a functionally equivalent Hu-B1.219 protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter an Hu-B1.219 coding sequence for a variety of ends including but not limited to alterations which modify processing and expression of the gene product. For example, mutations may be introduced using techniques which are well known in the art, e.g., site-directed mutagenesis, to insert new restriction sites, to alter glycosylation patterns, phosphorylation, etc.

In another embodiment of the invention, an Hu-B1.219 or a modified Hu-B1.219 sequence may be ligated to a heterologous sequence to encode a fusion protein. For example, for screening of peptide libraries for inhibitors or stimulators of Hu-B1.219 activity, it may be useful to encode a chimeric Hu-B1.219 protein expressing a heterologous epitope that is recognized by a commercially available antibody. A fusion protein may also be engineered to contain a cleavage site located between a Hu-B1.219 sequence and the heterologous protein sequence., so that the Hu-B1.219 may be cleaved away from the heterologous moiety.

In an alternate embodiment of the invention, the coding sequence of a Hu-B1.219 could be synthesized in whole or in part, using chemical methods well known in the art. See, for example, Caruthers et al., 1980, Nuc. Acids Res. Symp. Ser. 7:215–233; Crea and Horn, 180, Nuc. Acids Res. 9(10) :2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize an Hu-B1.219 amino acid sequence in whole or in part. For example, peptides can be synthesized by solid phase techniques, cleaved from the resin, and purified by preparative high performance liquid chromatography. (e.g., see Creighton, 1983, Proteins Structures And Molecular Principles, W. H. Freeman and Co., New York. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., New York., pp. 34–49).

In order to express a biologically active Hu-B1.219, the nucleotide sequence coding for Hu-B1.219, or a functional equivalent, is inserted into an appropriate expression vector, i.e., a vector which contains the necessary elements for the transcription and translation of the inserted coding sequence. The Hu-B1.219 gene products as well as host cells or cell lines transfected or transformed with recombinant Hu-B1.219 expression vectors can be used for a variety of purposes. These include but are not limited to generating antibodies (i.e., monoclonal or polyclonal) that competitively inhibit activity of an Hu-B1.219 and neutralize its activity; and antibodies that mimic the activity of Hu-B1.219 ligands in stimulating the receptor to transmit an intracellular signal. Anti-Hu-B1.219 antibodies may be used in detecting and quantifying expression of Hu-B1.219 levels in cells and tissues.

5.3. Expression Systems

Methods which are well known to those skilled in the art can be used to construct expression vectors containing the Hu-B1.219 coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York.

A variety of host-expression vector systems may be utilized to express the Hu-1.219 coding sequence. These include but are not limited to microorganisms such as bacteria transformed with recombinant bacteriophage DNA, plasmid DNA or cosmid DNA expression vectors containing the Hu-B1.219 coding sequence; yeast transformed with recombinant yeast expression vectors containing the Hu-B1.219 coding sequence; insect cell systems infected with recombinant virus expression vectors (e.c., baculovirus) containing the Hu-B 1.219 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Hu-B1.219 coding sequence; or animal cell systems The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage $\xi$, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Hu-B1.219 DNA, SV40-, BPV- and EBV-based vectors may be used with an appropriate selectable marker.

In bacterial systems a number of expression vectors may be advantageously selected depending upon the use intended for the Hu-B1.219 expressed. For example, when large quantities of Hu-B1.219 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the Hu-B1.219 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, New York., Vol. 153, pp. 516–544; Glover, 1986, DNA Cloning, Vol. II, IRL Press, Wash., D.C., Ch. 3; and Bitter, Heterologous Gene Expression in Yeast, Methods in Enzymology, Eds. Berger & Kimmel, Acad. Press, New York., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the Hu-B1.219 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9.

An alternative expression system which could be used to express Hu-B1.219 is an insect system. In one such system, *Autographa californica* nuclear polyhidrosis virus (AcNPV) is used as a vector to express foreign genes. The virus grows in *Spodoptera frugiperda* cells. The Hu-B1.219 coding sequence may be cloned into non-essential regions (for example the polyhedrin gene) of the virus and placed under control of an AcNPV promoter (for example the polyhedrin promoter). Successful insertion of the Hu-B1.219 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the Hu-B1.219 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Hu-B1.219 in infected hosts. (e.g., See Logan & Shenk, 1984, Proc. Natl. Acad. Sci. USA 81:3655–3659). Alternatively, the vaccinia 7.5K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Specific initiation signals may also be required for efficient translation of inserted Hu-B1.219 coding sequences. These signals include the ATG initiation codon and adjacent sequences. In cases where the entire Hu-B1.219 gene, including its own initiation codon and adjacent sequences, is inserted into the appropriate expression vector, no additional translational control signals may be needed. However, 4n cases where only a portion of the Hu-B1.219 coding sequence is inserted, exogenous translational control signals, including the ATG initiation codon, must be provided. Furthermore, the initiation codon must be in phase with the reading frame of the Hu-B1.219 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of several consensus N-glycosylation sites in the Hu-B1.219 extracellular domain support the possibility that proper modification may be important for Hu-B1.219 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the Hu-B1.219 may be engineered. Rather than using expression vectors which contain viral origins of replication, host cells can be transformed with the Hu-B1.219 DNA controlled by appropriate expression control elements (e.g., promoter, enhancer sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Hu-B1.219 on the cell surface. Such engineered cell lines are particularly useful in screening for ligands or drugs that affect Hu-B1.219 function.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk–, hgprt– or aprt– cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize Indole in place of tryptophan; hisD, which allows cells to utilize histinol in place of histidine (Hartman & Mulligan, 1988, Proc. Natl., Acad. Sci. USA 85:8047); and ODC (ornithine decarboxylase) which confers resistance to the ornithine decarboxylase inhibitor, 2-(difluoromethtyl)-DL-ornithine, DFMO (McConlogue L., 1987, In: Current Communications in Molecular Biology, Cold Spring Harbor Laboratory ed.).

5.4. Identification Cells that Express Hu-B1.219

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of Hu-B1.219 mRNA transcripts in the host cell; and (d) detection of the gene product as measured by immunoassay or by its biological activity. Prior to the identification of gene expression, the host cells may be first mutagenized in an effort to increase the level of expression of Hu-B1.219, especially in cell lines that produce low amounts of Hu-B1.219.

In the first approach, the presence of the Hu-B1.219 coding sequence inserted in the expression vector can be detected by DNA-DNA or DNA-RNA hybridization using probes comprising nucleotide sequences that are homologous to the Hu-B1.219 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Hu-B1.219 coding sequence is inserted within a marker gene sequence of the vector, recombinants containing the Hu-B1.219 coding sequence can be identified by the absence of the marker gene function. Alternatively, a marker gene can be placed in tandem with the Hu-B1.219 sequence under the control of the same or different promoter used to control the expression of the Hu-B1.219 coding sequence. Expression of the marker in response to induction or selection indicates expression of the Hu-B1.219 coding sequence.

In the third approach, transcriptional activity for the Hu-B1.219 coding region can be assessed by hybridization assays. For example, RNA can be isolated and analyzed by Northern blot using a probe homologous to the Hu-B1.219 coding sequence or particular portions thereof. Alternatively, total nucleic acids of the host cell may be extracted and assayed for hybridization to such probes.

In the fourth approach, the expression of the Hu-B1.219 protein product can be assessed immunologically, for example by Western blots, immunoassays such as radioimmunoprecipitation, enzyme-linked immunoassays and the like.

5.5. Uses of Hu-B1.219 Engineered Cell Lines

In an embodiment of the invention, the Hu-B1.219 receptor and/or cell lines that express the Hu-B1.219 receptor may be used to screen for antibodies, peptides, or other ligands that act as agonists or antagonists of the Hu-B1.219 receptor. For example, anti-Hu-B1.219 antibodies may be used to inhibit or stimulate receptor Hu-B1.219 function. Alternatively, screening of peptide libraries with recombinantly expressed soluble Hu-B1.219 protein or cell lines expressing Hu-B1.219 protein may be useful for identification of therapeutic molecules that function by inhibiting or stimulating the biological activity of Hu-B1.219. The uses of the Hu-B1.219 receptor and engineered cell lines, described in the subsections below, may be employed equally well for other members of the HR family.

In an embodiment of the invention, engineered cell lines which express most of the Hu-B1.219 coding region or its ligand binding domain or its ligand binding domain fused to another molecule such as the immunoglobulin constant region (Hollenbaugh and Aruffo, 1992, Current Protocols in Immunology, Unit 10.19; Aruffo et al., 1990, Cell 61:1303) may be utilized to produce a soluble receptor to screen and identify ligand antagonists as well as agonists. The soluble Hu-B1.219 protein or fusion protein may be used to identify a ligand in binding assays, affinity chromatography, immunoprecipitation, Western blot; and the like. Alternatively, the ligand binding domain of Hu-B1.219 may be fused to the coding sequence of the epidermal growth factor receptor transmembrane and cytoplasmic regions. This approach provides for the use of the epidermal growth factor receptor signal transduction pathway as a means for detecting ligands that bind to Hu-B1.219 in a manner capable of triggering an intracellular signal. Synthetic compounds, natural products, and other sources of potentially biologically active materials can be screened in a number of ways.

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that stimulate or inhibit the biological activity of receptors through their interactions with the given receptor.

Identification of molecules that are able to bind to the Hu-B1.219 may be accomplished by screening a peptide library with recombinant soluble Hu-B1.219 protein. Methods for expression and purification of Hu-B1.219 are described in Section 5.2, supra, and may be used to express recombinant full length Hu-B1.219 or fragments of Hu-B1.219 depending on the functional domains of interest. For example, the cytoplasmic and extracellular ligand binding domains of Hu-B1.219 may be separately expressed and used to screen peptide libraries.

To identify and isolate the peptide/solid phase support that interacts and forms a complex with Hu-B1.219, it is necessary to label or "tag" the Hu-B1.219 molecule. The Hu-B1.219 protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to Hu-B1.219 may be performed using techniques that are routine in the art. Alternatively, Hu-B1.219 expression vectors may be engineered to express a chimeric Hu-B1.219 protein containing an epitope for which a commercially available antibody exist. The epitope specific antibody may be tagged using methods well known in the art including labeling with enzymes, fluorescent dyes or colored or magnetic beads.

The "tagged" Hu-B1.219 conjugate is incubated with the random peptide library for 30 minutes to one hour at 22° C. to allow complex formation between Hu-B1.219 and peptide species within the library. The library is then washed to remove any unbound Hu-B1.219 protein. If Hu-B1.219 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3, 3', 4, 4∝-diaminobenzidine (DAB), respectively. After incubating for several minutes, the peptide/solid phase-Hu-B1.219 complex changes color, and can be easily identified and isolated physically under a dissecting microscope with a micromanipulator. If a fluorescent tagged Hu-B1.219 molecule has been used, complexes may be isolated by fluorescent activated sorting. If a chimeric Hu-B1.219 protein expressing a heterologous epitope has been used, detection of the peptide/Hu-B1.219 complex may be accomplished by using a labeled epitope specific antibody. Once isolated, the identity of the peptide attached to the solid phase support may be determined by peptide sequencing.

In addition to using soluble Hu-B1.219 molecules, in another embodiment, it is possible to detect peptides that bind to cell surface receptors using intact cells The use of intact cells is preferred for use with receptors that are multi-subunits or labile or with receptors that require the lipid domain of the cell membrane to be functional. Methods for generating cell lines expressing Hu-B1.219 are described in Section 5.3. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

Various procedures known in the art may be used for the production of antibodies to epitopes of the recombinantly produced Hu-B1.219 receptor. Such antibodies include but are not limited to polyclonal, monoclonal, chimeric, single chain, Fab fragments and fragments produced by an Fab expression library. Neutralizing antibodies i.e., those which compete for the ligand binding site of the receptor are especially preferred for diagnostics and therapeutics. Monoclonal antibodies that bind Hu-B1.219 may be radioactively labeled allowing one to follow their location and distribution in the body after injection. Radioisotope tagged antibodies may be used as a non-invasive diagnostic tool for imaging de novo cells of tumors and metastases.

Immunotoxins may also be designed which target cytotoxic agents to specific sites in the body. For example, high affinity Hu-B1.219 specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Hu-B1.219 expressing tumor cells.

For the production of antibodies, various host animals may be immunized by injection with the Hu-B1.219 protein including but not limited to rabbits, mice, rats, etc. Various adjuvants may be used to increase the immunological response, depending on the host species: including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to Hu-B1.219 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Hu-B1.219-specific single chain antibodies.

Antibody fragments which contain specific binding sites of Hu-B1.219 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Hu-B1.219.

5.6. Uses of Hu-B1.219 Polynucleotide

An Hu-B1.219 polynucleotide may be used for diagnostic and/or therapeutic purposes. For diagnostic purposes, an Hu-B1.29 polynucleotide may be used to detect Hu-B1.219 gene expression or aberrant Hu-B1.219 gene expression in disease states, e.g., chronic myelogenous leukemia. Included in the scope of the invention are oligonucleotide sequences, that include antisense RNA and DNA molecules and ribozymes, that function to inhibit translation of an Hu-B1.219.

5. 6. 1. Diagnostic Uses of An Hu-B1.219 Polynucleotide

An Hu-B1.219 polynucleotide may have a number of uses for the diagnosis of diseases resulting from aberrant expression of Hu-B1.219. For example, the Hu-B1.219 DNA sequence may be used in hybridization assays of biopsies or autopsies to diagnose abnormalities of Hu-B1.219 expression; e.g., Southern or Northern analysis, including in situ hybridization assays. Such techniques are well known in the art, and are in fact the basis of many commercially available diagnostic kits.

5. 6. 2. Therapeutic Uses of An Hu-B1.219 Polynucleotide

An Hu-B1.219 polynucleotide may be useful in the treatment of various abnormal conditions. By introducing gene sequences into cells, gene therapy can be used to treat conditions in which the cells do not proliferate or differentiate normally due to underexpression of normal Hu-B1.219 or expression of abnormal/inactive Hu-B1.219. In some instances, the polynucleotide encoding an Hu-B1.219 is intended to replace or act in the place of a functionally deficient endogenous gene. Alternatively, abnormal conditions characterized by overproliferation can be treated using the gene therapy techniques described below.

Abnormal cellular proliferation is an important component of a variety of disease states. Recombinant gene therapy vectors, such as viral vectors, may be engineered to express variant, signalling incompetent forms of Hu-B1.219 which may be used to inhibit the activity of the naturally occurring endogenous Hu-B1.219. A signalling incompetent form may be, for example, a truncated form of the protein that is lacking all or part of its signal transduction domain. Such a truncated form may participate in normal binding to a substrate but lack signal transduction activity. Thus recombinant gene therapy vectors may be used therapeutically for treatment of diseases resulting from aberrant expression or activity of an Hu-B1.219. Accordingly, the invention provides a method of inhibiting the effects of signal transduction by an endogenous Hu-B1.219 protein in a cell comprising delivering a DNA molecule encoding a signalling incompetent form of the Hu-B1.219 protein to the cell so that the signalling incompetent Hu-B1.219 protein is produced in the cell and competes with the endogenous Hu-B1.219 protein for access to molecules in the Hu-B1.219 protein signalling pathway which activate or are activated by the endogenous Hu-B1.219 protein.

Expression vectors derived from viruses such as retroviruses, vaccinia virus, adeno-associated virus, herpes viruses, or bovine papilloma virus, may be used for delivery of recombinant Hu-B1.219 into the targeted cell population. Methods which are well known to those skilled in the art can be used to construct recombinant viral vectors containing an Hu-B1.219 polynucleotide sequence. See, for example, the techniques described in Maniatis et al., 1989, Molecular Cloning A Laboratory Manual, Cold Spring Harbor Laboratory, New York and Ausubel et al., 1989, Current Protocols in Molecular Biology, Greene Publishing Associates and Wiley Interscience, New York. Alternatively, recombinant Hu-B1.219 molecules can be reconstituted into liposomes for delivery to target cells.

Oligonucleotide sequences, that include anti-sense RNA and DNA molecules and ribozymes that function to inhibit the translation of an Hu-B1.219 mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an Hu-B1.219 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of Hu-B1.219 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' 0-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of an Hu-B1.219 polynucleotide in a cell ex vivo, i.e., for use in autologous cell therapy, the use of a vector such as a virus, retrovirus, phage or plasmid, etc. or techniques such as electroporation which may be used in vivo or ex vivo.

6. Example Molecular Cloning of A Novel Hematopoietin Receptor Complementary DNA

6.1. Materials and Methods

6.1.1. Northern Blot Analysis

In order to study the expression of the Hu-B1.219 gene, Northern blots containing RNA obtained from a variety of human tissues (Clontech, Palo Alto, Calif.) were hybridized with a radiolabeled 530 base pair (bp) DNA probe corresponding to nucleotides #578 through 1107 (see FIG. 2A–2E). Briefly, the blots were prehybridized at 42° C. for 3–6 hours in a solution containing 5×SSPE, 10×Denhardt's solution, 100 µg/ml freshly denatured, sheared salmon sperm DNA, 50% formamide (freshly deionized) and 2% SDS. The radiolabeled probe was heat denatured and added to the prehybridization mix and allowed to hybridize at 42° C. for 18–24 hours with constant shaking. The blots were rinsed in 2×SSC, 0.05% SDS several times at room temperature before being transferred to a wash solution containing 0.1×SSC, 0.1% SDS and agitated at 50° C. for 40 minutes The blots were then covered with plastic wrap, mounted on Whatman paper and exposed to x-ray film at −70° C. using an intensifying screen.

6.1.2. Reverse Transcription/Polymerase Chain Reaction (RT/PCR)

Total RNA was isolated using standard laboratory procedures (Sambrook et al., 1989, Molecular Cloning, A Laboratory Manual, Cold Spring Harbor Laboratory, New York.). Approximately 1 µg of total RNA was reverse transcribed and the cDNA was amplified by PCR (Perkin Elmer, Norwalk, Conn.). The PCR amplification conditions were the same for Hu-B1.219 and Form 1 expression analysis. They were: 94° C. for 30 sec, 60° C. for 30 sec, 72° C. for 30 sec for a total of 40 cycles. The amplified products (224 bp for Hu-B1.219 and 816 bp for Form 1) were resolved by agarose gel electrophoresis and visualized by ethidium bromide staining. The Hu-B1.219 amplimers were GGTTTG-CATATGGAAGTC (SEQ ID No: 2) (upper) and CCT-GAACCATCCAGTCTCT (SEQ ID No: 2) (lower). The Form 1 specific amplimers were GACTCATTGTGCAGT-GTTCAG (SEQ ID No: 3(upper) and TAGTGGAGG-GAGGGTCAGCAG (SEQ ID No: 4) (lower). The upper amplimer was commonly shared by all 3 forms, whereas the lower amplimer was Form 1-specific.

6.2. Results

A number of cDNA clones were isolated from a human fetal liver cDNA library (Clontech, Palo Alto, Calif.), and the DNA sequences of several of these clones were determined. These clones (Hu-B1.219 #4, #33, #34, #1, #36, #8, #55, #60, #3, #57, #62) contained overlapping sequences, which were then compiled into a contiguous nucleotide sequence. Both the cDNA sequence and predicted protein sequence from the cDNA are shown in FIG. 2A–2G. This cDNA sequence contains two FN III domains, each containing a "WS box", which are characteristic of genes of the HR family. However, the Hu-B1.219 sequence is not identical to any known gene. Thus, this cDNA represents a novel member of the HR gene family, herein referred to as Hu-B1.219 (Table 1).

TABLE 1

Cytokine Receptor Gene FN III Domain Sizes (bp)

| Gene | Human | Mouse | Rat |
|---|---|---|---|
| Hu-B1.219(5') | 273 | | |
| Hu-B1.219(3') | 282 | | |
| IL-2Rβ | 291 | 288 | 291 |
| IL-2Rγ | 273 | | |
| IL-3Rα | 246 | 252 | |
| IL-3RβAic2a | | 306 and 273 | |
| IL-3RβAic2b | 306 and 282 | 303 and 276 | |
| IL-4R | 294 | | 291 |
| IL-5Rα | 276 | 273 | |
| IL-6R | 288 | 285 | |
| gp130 | 288 | 291 | 288 |
| IL-7R | | 294 | |
| IL-9R | 321 | 321 | |
| mpl | | 270 | |
| G-CSFR | 300 | 297 | |
| GM-CSFR | 288 | | |
| CNTFR | 282 | | 285 |
| PRLR | | | 288 |
| EPOR | 288 | 285 | 288 |
| LIFR-1 | 321 and 297 | | |

Based on the sequence of Hu-B1.219 presented in FIG. 2A–2G, the translation initiation site appears at position #97. The sequence encodes an open reading frame up to and including nucleotide #2970. It is believed that the sequence between nucleotides #2614 and #2691 encodes a transmembrane domain. The complete sequence encodes a protein of 958 amino acids.

However, the sequence in FIG. 2A–2E represents only one form of Hu-B1.219 cDNA sequence, herein referred to as Form 1. This is because additional lambda clones were discovered that contained different sequences near the 3' end known as Form 2 and Form 3. All three forms contain the identical sequence up to and including nucleotide #2770, then they diverge at nucleotide #2771 and beyond (FIG. 3A). An alignment of deduced amino acid sequences of all three forms corresponding to the 3' end from #2771 until a stop codon is shown in FIG. 3B. Two of the originally isolated lambda clones, #36 and #8, contain the 3' end sequences of Form 1 and Form 2, respectively. These three forms of Hu-B1.219 may derive from a common precursor mRNA by an alternative splicing mechanism.

It is noteworthy that the DNA sequence of Form 1 from nucleotide #2771 to the end is 98% identical to a human retrotransposon sequence that is thought to be derived from a human endogenous retroviral DNA sequence (Singer, 1982, Cell 28:433; Weiner et al., 1986, Ann. Rev. Biochem. 55:631; Lower et al., 1993, Proc. Natl. Acad. Sci. USA 90:4480). In order to examine the expression of the different forms of cDNA, RT/PCR was performed using several human cell lines. The results in Table 2 show that Form 1 was expressed as RNA in K-562 cells and in a human fetal liver cDNA preparation. Since Hu-B1.219 was cloned from human fetal liver cDNA library, this served as a positive control. However, with respect to several other human cell lines, Form 1 was not detected, whereas Hu-B1.219 expression was positive. For example, Form 1 was not expressed in KGla cells, but Form 3 was expressed. Thus, it is possible that these three forms of Hu-B1.219 are not expressed simultaneously in the same cells. There may be selective expression of certain forms in particular cell populations.

TABLE 2

RT/PCR Analysis of Hu-B1.219 Expression

| Cell Lines | Hu-B1.219* | Form 1Δ | Form 3Δ |
|---|---|---|---|
| MRC5 (Lung fibroblast) | ++ | +/− | + |
| KG1a (lymphoblast) | + | − | ++ |
| Raji (B cell lymphoma) | + | − | + |
| Kit 225/K6 (T cell) | +++ | − | + |
| K562 (myelogenous leukemia) | ++++ | +++ | ++++ |
| Human Fetal Liver (positive control) | +++ | +++ | +++ |

\* - Analysis by Northern blots
Δ - Analysis by RT/PCR

Various human tissue RNA were probed with a radiolabelled Hu-B1.219 fragment corresponding to nucleotide numbers from #578 to #1107 as disclosed in FIG. 2A–2G for Northern blot analyses. Two different size mRNAs were detected. This result suggests that there may be another homologous gene or there is alternative splicing of a single RNA transcript. Hu-B1.219 expression was by far the strongest in human fetal tissues, particularly the liver and lung. Trace levels were found in several adult tissues. Interestingly, a chronic myelogenous leukemia cell line, K562, was strongly positive for its expression, while some expression was also detected in A549 cells, a lung carcinoma cell line (Table 3).

TABLE 3

SUMMARY OF NORTHERN BLOT ANALYSIS OF Hu-B1.219 GENE EXPRESSION

| Human Tissues/cell lines | | Expression |
|---|---|---|
| fetal | brain | − |
| | lung | +++ |
| | liver | +++++ |
| | kidney | + |
| adult | heart | + |
| | brain | − |
| | placenta | +/− |
| | lung | + |
| | liver | + |
| | skeletal muscle | − |
| | kidney | +/− |
| | pancreas | − |
| | spleen | − |
| | thymus | − |
| | prostate | − |
| | testis | − |
| | ovary | + |
| | small intestine | − |
| | colon | − |
| | peripheral blood leukocytes | − |
| cancer | HL-60 | − |
| | HeLa | − |
| | K-562 | +++ |
| | MOLT-4 | − |
| | Raji | − |
| | SW480 | − |
| | A549 | + |
| | G361 | − |

Taken together, the data indicates that the Hu-B1.219 cDNA clone represents a new member of the human hematopoietin receptor family. A summary of the data that supports this conclusion is as follows:

1. The Hu-B1.219 DNA and protein sequences do not fully match any known sequences in the corresponding computer data bases.
2. Hu-B1.219 shares certain DNA sequence homology with the IL-6R and IL-4R.
3. It shares certain protein homology with G-CSFR, IL-6R, IL-3R beta chain, gp130, IL-12R, and LIFR.
4. It contains two "WS box" motifs with the correct spacing of conserved amino acids in the FN III domains (see FIG. 4).
5. It contains an amphipathic sequence in block 3 of the FN III domains (see FIG. 5).
6. It contains alternating hydrophobic and basic amino acids in block 6 of the FN III domains (see FIG. 6).
7. It contains conserved cysteines in these cysteine rich regions upstream of the FN III domains.
8. It was originally cloned from a hematopoietic tissue, fetal liver.
9. It is expressed by certain fetal tissues.

7. Deposit of Microorganisms

The following organisms were deposited with the American Type Culture Collection (ATCC), 12301 Parklawn Drive, Rockville, Md. 20852.

| Strain Designation | Accession No. |
|---|---|
| HuB1.219, #1 | 75885 |
| HuB1.219, #4 | 75886 |
| HuB1.219, #8 | 75887 |
| HuB1.219, #33 | 75888 |
| HuB1.219, #34 | 75889 |
| HuB1.219, #36 | 75890 |
| HuB1.219, #55 | |
| HuB1.219, #60 | |
| HuB1.219, #3 | |
| HuB1.219, #57 | |
| HuB1.219, #62 | |

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. An isolated polynucleotide, comprising a nucleotide sequence that hybridizes under stringent conditions to a second polynucleotide having a nucleotide sequence as shown in SEQ ID NO: 6 between residues #1 and #2770, or to the complementary sequence of the second polynucleotide, and which isolated polynucleotide encodes a naturally-occurring receptor polypeptide.

2. The isolated polynucleotide of claim 1 that encodes a soluble receptor polypeptide.

3. The isolated polynucleotide of claim 1 that encodes a cell membrane-associated receptor polypeptide.

4. An isolated polynucleotide, comprising a nucleotide sequence that hybridizes under stringent conditions to a second polynucleotide having a nucleotide sequence as shown in SEQ ID NO: 6, or to the complementary sequence of the second polynucleotide, and which isolated polynucleotide encodes a naturally-occurring receptor polypeptide.

5. An isolated polynucleotide, comprising a nucleotide sequence that hybridizes under stringent conditions to a second polynucleotide having a nucleotide sequence as shown in SEQ ID NO: 6 in which the nucleotide sequence corresponding to residue #2751 to the 3' end is replaced by the nucleotide sequence of SEQ ID NO: 13, or to the complementary sequence of the second polynucleotide, and which isolated polynucleotide encodes a naturally-occurring receptor polypeptide.

6. An isolated polynucleotide, comprising a nucleotide sequence that hybridizes under stringent conditions to a second polynucleotide having a nucleotide sequence as shown in SEQ ID NO: 6 in which the nucleotide sequence corresponding to residue #2751 to the 3' end is replaced by the nucleotide sequence of SEQ ID NO: 16, or to the complementary sequence of the second polynucleotide, and which isolated polynucleotide encodes a naturally-occurring receptor polypeptide.

7. An isolated polynucleotide, comprising a nucleotide sequence that hybridizes under stringent conditions to a second polynucleotide having a nucleotide sequence as shown in SEQ ID NO: 6 between residues #1 and #2770, or to the complementary sequence of the second polynucleotide.

8. A genetically-engineered host cell containing the polynucleotide of claim 7 or progeny thereof.

9. An isolated polynucleotide, comprising a nucleotide sequence that encodes a polypeptide comprising the amino acid sequence as shown in SEQ ID NO: 8 from residue #3 to #887.

10. The isolated polynucleotide of claim 9 in which the nucleotide sequence is shown in SEQ ID NO: 6.

11. The isolated polynucleotide of claim 9 that encodes a naturally-occurring human variant receptor polypeptide having the amino acid sequence as shown in SEQ ID NO: 8 from residue #3 to #887 which is immediately followed by the amino acid sequence in SEQ ID NO: 14.

12. The isolated polynucleotide to claim 11 in which the nucleotide sequence is shown in SEQ ID NO: 6 except that the nucleotide sequence corresponding to residue #2751 to the 3' end is replaced by the nucleotide sequence of SEQ ID NO: 13.

13. The isolated polynucleotide of claim 9 that encodes a naturally-occurring human variant receptor polypeptide having the amino acid sequence as shown in SEQ ID NO: 8 from residue #3 to #887 which is immediately followed by the amino acid sequence in SEQ ID NO: 17.

14. The isolated polynucleotide of claim 13 in which the nucleotide sequence is shown in SEQ ID NO: 6 except that the nucleotide sequence corresponding to residue #2751 to the 3' end is replaced by the nucleotide sequence of SEQ ID NO: 16.

15. An isolated polynucleotide, comprising a nucleotide sequence that encodes an extracellular domain of a polypeptide having the amino acid sequence as shown in SEQ ID NO: 8.

16. The isolated polynucleotide of claim 15, in which the extracellular domain comprises the amino acid sequence of SEQ ID NO: 25.

17. The isolated polynucleotide of claim 15, in which the extracellular domain comprises the amino acid sequence of SEQ ID NO: 30.

18. The isolated polynucleotide of claim 15, in which the extracellular domain comprises the amino acid sequence of SEQ ID NO: 31.

19. The isolated polynucleotide of claim 15, in which the extracellular domain comprises the amino acid sequence of SEQ ID NO: 8 from residue #266 to #278.

20. The isolated polynucleotide of claim 15, in which the extracellular domain comprises the amino acid sequence of SEQ ID NO: 8 from residue #3 to about #841.

21. An isolated non-naturally-occurring polynucleotide, comprising a nucleotide sequence that encodes a polypeptide comprising the amino acid sequence as shown in SEQ ID NO: 8 from residue #3 to #887.

22. The polynucleotide of claim 21 in which the nucleotide sequence is shown in SEQ ID NO: 6.

23. The polynucleotide of claim 21 that encodes a naturally-occurring human variant receptor polypeptide having the amino acid sequence as shown in SEQ ID NO: 8 from residue #3 to #887 which is immediately followed by the amino acid sequence in SEQ ID NO: 14.

24. The polynucleotide of claim 23 in which the nucleotide sequence is shown in SEQ ID NO: 6 except that the nucleotide sequence corresponding to residue #2751 to the 3' end is replaced by the nucleotide sequence of SEQ ID NO: 13.

25. The polynucleotide of claim 21 that encodes a naturally-occurring human variant receptor polypeptide having the amino acid sequence as shown in SEQ ID NO: 8 from residue #3 to #887 which is immediately followed by the amino acid sequence in SEQ ID NO: 17.

26. The polynucleotide of Claim 25 in which the nucleotide sequence is shown in SEQ ID NO: 6 except that the nucleotide sequence corresponding to residue #2751 to the 3' end is replaced by the nucleotide sequence of SEQ ID NO: 16.

27. An isolated non-naturally-occurring polynucleotide, comprising a nucleotide sequence that encodes an extracellular domain of a polypeptide having the amino acid sequence as shown in SEQ ID NO: 8.

28. The polynucleotide of claim 27, in which the extracellular domain comprises the amino acid sequence of SEQ ID NO: 25.

29. The polynucleotide of claim 27 in which the extracellular domain comprises the amino acid sequence of SEQ ID NO: 30.

30. The polynucleotide of claim 27, in which the extracellular domain comprises the amino acid sequence of SEQ ID NO: 31.

31. The polynucleotide of claim 27, in which the extracellular domain comprises the amino acid sequence of SEQ ID NO: 8 from residue #266 to #278.

32. The polynucleotide of Claim 27, in which the extracellular domain comprises the amino acid sequence of SEQ ID NO: 8 from residue #3 to about #841.

33. The polynucleotide of any of claims 1 to 32 which is DNA.

34. The polynucleotide of claim 33 which is cDNA.

35. The polynucleotide of claim 33 which exists as a double helix.

36. The polynucleotide of any of claims 1 to 32 which is RNA.

37. A recombinant vector containing the polynucleotide of any of claims 1 to 32.

38. A recombinant expression vector containing the polynucleotide of any of claims 1 to 6 in which the nucleotide sequence of the polynucleotide is operatively associated with a regulatory nucleotide sequence that controls expression of the polynucleotide in a host cell.

39. A recombinant expression vector containing the polynucleotide of any of claims 9 to 32 in which the nucleotide sequence of the polynucleotide is operatively associated with a regulatory nucleotide sequence that controls expression of the polynucleotide in a host cell.

40. A genetically-engineered host cell containing the polynucleotide of any of claims 1 to 6 or progeny thereof.

41. A genetically-engineered host cell containing the polynucleotide of any of claims 9 to 32 or progeny thereof.

42. A genetically-engineered host cell containing the polynucleotide of any of claims 1 to 6 in which the nucleotide sequence of the polynucleotide is operatively associated with a regulatory nucleotide sequence that controls expression of the polynucleotide in the host cell, or progeny thereof.

43. The genetically-engineered host cell of claim 42 which is a prokaryote.

44. A method for producing a polypeptide, comprising:

(a) culturing the genetically-engineered host cell of claim 43; and (b) recovering the polypeptide from the cultured host cell or its culture medium.

45. The genetically-engineered host cell of Claim 42 which is an eukaryote.

46. A method for producing a polypeptide, comprising:

(a) culturing the genetically engineered host cell of claim 45; and (b) recovering the polypeptide from the cultured host cell or its culture medium.

47. A genetically-engineered host cell containing the polynucleotide of any of claims 9 to 32 in which the nucleotide sequence of the polynucleotide is operatively associated with a regulatory nucleotide sequence that controls expression of the polynucleotide in the host cell, or progeny thereof.

48. The genetically-engineered host cell of claim 47 which is a prokaryote.

49. A method for producing a polypeptide, comprising:

(a) culturing the genetically-engineered host cell of claim 48; and (b) recovering the polypeptide from the cultured host cell or its culture medium.

50. The genetically-engineered host cell of claim 47 which is an eukaryote.

51. A method for producing a polypeptide, comprising:

(a) culturing the genetically engineered host cell of claim 50; and (b) recovering the polypeptide from the cultured host cell or its culture medium.

52. The polynucleotide of claim 21 or 27 in which the polynucleotide is chemically synthesized.

53. The isolated polynucleotide of claim 9 that encodes a polypeptide comprising the amino acid sequence shown in SEQ ID NO: 8 from residue #3 to #960.

54. The isolated polynucleotide of claim 21 that encodes a polypeptide comprising the amino acid sequence shown in SEQ ID NO: 8 from residue #3 to #960.

* * * * *

UNITED STATES PATENT AND TRADEMARK OFFICE
CERTIFICATE OF CORRECTION

PATENT NO. : 5,763,211

DATED : 6/9/98

INVENTOR(S) : Snodgrass et al.

It is certified that error appears in the above-identified patent and that said Letters Patent is hereby corrected as shown below:

Column 15, line 20-21, delete "Figure 2A-2E" and insert therefor --Figure 2A-2G--.

Column 16, line 32, delete "Figure 2A-2E" and insert therefor --Figure 2A-2G--.

Signed and Sealed this

Second Day of March, 1999

*Attest:*

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.   : 5,763,211
DATED        : June 9, 1998
INVENTOR(S)  : Snodgrass et al.

It is certified that error appears in the above-identified patent and that said Letters Patent is hereby corrected as shown below:

First page [54] Title,
Line 2, after "HEMATOPOIETIN" add -- RECEPTOR --

Column 1,
Line 66, delete "hesmatopoietic" and insert therefor -- hematopoietic --.

Column 3,
Line 13, delete "(SEQ ID No: 8)" and insert therefor -- (SEQ ID No: 10) --.
Line 14, after "16" insert --)--.
Line 18, after "19" insert --)--.
Line 26, delete "(SEQ ID No: 30)" and insert therefor -- (SEQ ID No: 24)--.
Line 26, delete "(SEQ ID No: 31)" and insert therefor -- (SEQ ID No: 25)--.
Line 29, delete "(SEQ ID No: 21)" and insert therefor -- (SEQ ID No: 27)--.

Column 4,
Line 40, delete "cNA" and insert therefor -- cDNA --.
Line 45, delete "CDNA" and insert therefor -- cDNA --.

Column 6,
Line 47, delete "Hu-1.219" and insert therefor -- Hu-B1.219 --.

Column 7,
Line 48, after Bitter," add -- 1987, --.

Column 8,
Line 20, delete "Viol" and insert therefor -- Virol --.
Line 45, delete "4n" and insert therefor -- in --.

Column 11,
Line 50, delete "3, 3',4, 4∝–diaminobenzidine" and insert therefor -- 3, 3',4, 4' -diaminobenzidine --.

UNITED STATES PATENT AND TRADEMARK OFFICE
CERTIFICATE OF CORRECTION

PATENT NO.  : 5,763,211
DATED       : June 9, 1998
INVENTOR(S) : Snodgrass et al It is certified that error appears in the above-identified patent and that said Letters Patent is hereby corrected as shown below:

Column 13,
Line 20, delete "Hu-B1.29" and insert therefor -- Hu-B1.219 --.

Column 15,
Line 15, delete "30" before "6.1.1".
Line 48, delete "(SEQ ID No: 2)" and insert therefor -- (SEQ ID No: 3) --.

Signed and Sealed this

Fourteenth Day of August, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:1:

Trp Ser Xaa Trp Ser
1               5

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GGTTTGCATA TGGAAGTC                                                        18

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CCTGAACCAT CCAGTCTCT                                                  19

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GACTCATTGT GCAGTGTTCA G                                         21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

-continued

TAGTGGAGGG AGGGTCAGCA G                                             21

( 2 ) INFORMATION FOR SEQ ID NO:6:

( i ) SEQUENCE CHARACTERISTICS:
        ( A ) LENGTH: 2991 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 1..2991

( x i ) SEQUENCE DESCRIPTION: SEQ ID NO:6:

| GCG | CGC | GCG | ACG | CAG | GTG | CCC | GAG | CCC | CGG | CCC | GCG | CCC | ATC | TCT | GCC | 48 |
|---|---|---|---|---|---|---|---|---|---|---|---|---|---|---|---|---|
| Ala | Arg | Ala | Thr | Gln | Val | Pro | Glu | Pro | Arg | Pro | Ala | Pro | Ile | Ser | Ala | |
| 1 | | | | 5 | | | | | 10 | | | | | 15 | | |

| TTC | GGT | CGA | GTT | GGA | CCC | CCG | GAT | CAA | GGT | GTA | CTT | CTC | TGA | AGT | AAG | 96 |
|---|---|---|---|---|---|---|---|---|---|---|---|---|---|---|---|---|
| Phe | Gly | Arg | Val | Gly | Pro | Pro | Asp | Gln | Gly | Val | Leu | Leu | * | Ser | Lys | |
| | | | 20 | | | | | 25 | | | | | | 30 | | |

| ATG | ATT | TGT | CAA | AAA | TTC | TGT | GTG | GTT | TTG | TTA | CAT | TGG | GAA | TTT | ATT | 144 |
|---|---|---|---|---|---|---|---|---|---|---|---|---|---|---|---|---|
| Met | Ile | Cys | Gln | Lys | Phe | Cys | Val | Val | Leu | Leu | His | Trp | Glu | Phe | Ile | |
| | | 35 | | | | | 40 | | | | | 45 | | | | |

| TAT | GTG | ATA | ACT | GCG | TTT | AAC | TTG | TCA | TAT | CCA | ATT | ACT | CCT | TGG | AGA | 192 |
|---|---|---|---|---|---|---|---|---|---|---|---|---|---|---|---|---|
| Tyr | Val | Ile | Thr | Ala | Phe | Asn | Leu | Ser | Tyr | Pro | Ile | Thr | Pro | Trp | Arg | |
| | 50 | | | | | 55 | | | | | 60 | | | | | |

| TTT | AAG | TTG | TCT | TGC | ATG | CCA | CCA | AAT | TCA | ACC | TAT | GAC | TAC | TTC | CTT | 240 |
|---|---|---|---|---|---|---|---|---|---|---|---|---|---|---|---|---|
| Phe | Lys | Leu | Ser | Cys | Met | Pro | Pro | Asn | Ser | Thr | Tyr | Asp | Tyr | Phe | Leu | |
| 65 | | | | | 70 | | | | | 75 | | | | | 80 | |

| TTG | CCT | GCT | GGA | CTC | TCA | AAG | AAT | ACT | TCA | AAT | TCG | AAT | GGA | CAT | TAT | 288 |
|---|---|---|---|---|---|---|---|---|---|---|---|---|---|---|---|---|
| Leu | Pro | Ala | Gly | Leu | Ser | Lys | Asn | Thr | Ser | Asn | Ser | Asn | Gly | His | Tyr | |
| | | | | 85 | | | | | 90 | | | | | 95 | | |

| GAG | ACA | GCT | GTT | GAA | CCT | AAG | TTT | AAT | TCA | AGT | GGT | ACT | CAC | TTT | TCT | 336 |
|---|---|---|---|---|---|---|---|---|---|---|---|---|---|---|---|---|
| Glu | Thr | Ala | Val | Glu | Pro | Lys | Phe | Asn | Ser | Ser | Gly | Thr | His | Phe | Ser | |
| | | | 100 | | | | | 105 | | | | | 110 | | | |

| AAC | TTA | TCC | AAA | GCA | ACT | TTC | CAC | TGT | TGC | TTT | CGG | AGT | GAG | CAA | GAT | 384 |
|---|---|---|---|---|---|---|---|---|---|---|---|---|---|---|---|---|
| Asn | Leu | Ser | Lys | Ala | Thr | Phe | His | Cys | Cys | Phe | Arg | Ser | Glu | Gln | Asp | |
| | | 115 | | | | | 120 | | | | | 125 | | | | |

| AGA | AAC | TGC | TCC | TTA | TGT | GCA | GAC | AAC | ATT | GAA | GGA | AGG | ACA | TTT | GTT | 432 |
|---|---|---|---|---|---|---|---|---|---|---|---|---|---|---|---|---|
| Arg | Asn | Cys | Ser | Leu | Cys | Ala | Asp | Asn | Ile | Glu | Gly | Arg | Thr | Phe | Val | |
| | 130 | | | | | 135 | | | | | 140 | | | | | |

| TCA | ACA | GTA | AAT | TCT | TTA | GTT | TTT | CAA | CAA | ATA | GAT | GCA | AAC | TGG | AAC | 480 |
|---|---|---|---|---|---|---|---|---|---|---|---|---|---|---|---|---|
| Ser | Thr | Val | Asn | Ser | Leu | Val | Phe | Gln | Gln | Ile | Asp | Ala | Asn | Trp | Asn | |
| 145 | | | | | 150 | | | | | 155 | | | | | 160 | |

| ATA | CAG | TGC | TGG | CTA | AAA | GGA | GAC | TTA | AAA | TTA | TTC | ATC | TGT | TAT | GTG | 528 |
|---|---|---|---|---|---|---|---|---|---|---|---|---|---|---|---|---|
| Ile | Gln | Cys | Trp | Leu | Lys | Gly | Asp | Leu | Lys | Leu | Phe | Ile | Cys | Tyr | Val | |
| | | | | 165 | | | | | 170 | | | | | 175 | | |

| GAG | TCA | TTA | TTT | AAG | AAT | CTA | TTC | AGG | AAT | TAT | AAC | TAT | AAG | GTC | CAT | 576 |
|---|---|---|---|---|---|---|---|---|---|---|---|---|---|---|---|---|
| Glu | Ser | Leu | Phe | Lys | Asn | Leu | Phe | Arg | Asn | Tyr | Asn | Tyr | Lys | Val | His | |
| | | | 180 | | | | | 185 | | | | | 190 | | | |

| CTT | TTA | TAT | GTT | CTG | CCT | GAA | GTG | TTA | GAA | GAT | TCA | CCT | CTG | GTT | CCC | 624 |
|---|---|---|---|---|---|---|---|---|---|---|---|---|---|---|---|---|
| Leu | Leu | Tyr | Val | Leu | Pro | Glu | Val | Leu | Glu | Asp | Ser | Pro | Leu | Val | Pro | |
| | | 195 | | | | | 200 | | | | | 205 | | | | |

| CAA | AAA | GGC | AGT | TTT | CAG | ATG | GTT | CAC | TGC | AAT | TGC | AGT | GTT | CAT | GAA | 672 |
|---|---|---|---|---|---|---|---|---|---|---|---|---|---|---|---|---|
| Gln | Lys | Gly | Ser | Phe | Gln | Met | Val | His | Cys | Asn | Cys | Ser | Val | His | Glu | |
| | 210 | | | | | 215 | | | | | 220 | | | | | |

| TGT | TGT | GAA | TGT | CTT | GTG | CCT | GTG | CCA | ACA | GCC | AAA | CTC | AAC | GAC | ACT | 720 |
|---|---|---|---|---|---|---|---|---|---|---|---|---|---|---|---|---|
| Cys | Cys | Glu | Cys | Leu | Val | Pro | Val | Pro | Thr | Ala | Lys | Leu | Asn | Asp | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| CTC | CTT | ATG | TGT | TTG | AAA | ATC | ACA | TCT | GGT | GGA | GTA | ATT | TTC | CGG | TCA | 768 |
| Leu | Leu | Met | Cys | Leu | Lys | Ile | Thr | Ser | Gly | Gly | Val | Ile | Phe | Arg | Ser | |
| | | | | 245 | | | | 250 | | | | | | 255 | | |
| CCT | CTA | ATG | TCA | GTT | CAG | CCC | ATA | AAT | ATG | GTG | AAG | CCT | GAT | CCA | CCA | 816 |
| Pro | Leu | Met | Ser | Val | Gln | Pro | Ile | Asn | Met | Val | Lys | Pro | Asp | Pro | Pro | |
| | | | 260 | | | | | 265 | | | | | 270 | | | |
| TTA | GGT | TTG | CAT | ATG | GAA | ATC | ACA | GAT | GAT | GGT | AAT | TTA | AAG | ATT | TCT | 864 |
| Leu | Gly | Leu | His | Met | Glu | Ile | Thr | Asp | Asp | Gly | Asn | Leu | Lys | Ile | Ser | |
| | | 275 | | | | | 280 | | | | | 285 | | | | |
| TGG | TCC | AGC | CCA | CCA | TTG | GTA | CCA | TTT | CCA | CTT | CAA | TAT | CAA | GTG | AAA | 912 |
| Trp | Ser | Ser | Pro | Pro | Leu | Val | Pro | Phe | Pro | Leu | Gln | Tyr | Gln | Val | Lys | |
| | 290 | | | | | 295 | | | | | 300 | | | | | |
| TAT | TCA | GAG | AAT | TCT | ACA | ACA | GTT | ATC | AGA | GAA | GCT | GAC | AAG | ATT | GTC | 960 |
| Tyr | Ser | Glu | Asn | Ser | Thr | Thr | Val | Ile | Arg | Glu | Ala | Asp | Lys | Ile | Val | |
| 305 | | | | | 310 | | | | | 315 | | | | | 320 | |
| TCA | GCT | ACA | TCC | CTG | CTA | GTA | GAC | AGT | ATA | CTT | CCT | GGG | TCT | TCG | TAT | 1008 |
| Ser | Ala | Thr | Ser | Leu | Leu | Val | Asp | Ser | Ile | Leu | Pro | Gly | Ser | Ser | Tyr | |
| | | | | 325 | | | | | 330 | | | | | 335 | | |
| GAG | GTT | CAG | GTG | AGG | GGC | AAG | AGA | CTG | GAT | GGC | CCA | GGA | ATC | TGG | AGT | 1056 |
| Glu | Val | Gln | Val | Arg | Gly | Lys | Arg | Leu | Asp | Gly | Pro | Gly | Ile | Trp | Ser | |
| | | | 340 | | | | | 345 | | | | | 350 | | | |
| GAC | TGG | AGT | ACT | CCT | CGT | GTC | TTT | ACC | ACA | CAA | GAT | GTC | ATA | TAC | TTT | 1104 |
| Asp | Trp | Ser | Thr | Pro | Arg | Val | Phe | Thr | Thr | Gln | Asp | Val | Ile | Tyr | Phe | |
| | | 355 | | | | | 360 | | | | | 365 | | | | |
| CCA | CCT | AAA | ATT | CTG | ACA | AGT | GTT | GGG | TCT | AAT | GTT | TCT | TTT | CAC | TGC | 1152 |
| Pro | Pro | Lys | Ile | Leu | Thr | Ser | Val | Gly | Ser | Asn | Val | Ser | Phe | His | Cys | |
| | 370 | | | | | 375 | | | | | 380 | | | | | |
| ATC | TAT | AAG | AAG | GAA | AAC | AAG | ATT | GTT | CCC | TCA | AAA | GAG | ATT | GTT | TGG | 1200 |
| Ile | Tyr | Lys | Lys | Glu | Asn | Lys | Ile | Val | Pro | Ser | Lys | Glu | Ile | Val | Trp | |
| 385 | | | | | 390 | | | | | 395 | | | | | 400 | |
| TGG | ATG | AAT | TTA | GCT | GAG | AAA | ATT | CCT | CAA | AGC | CAG | TAT | GAT | GTT | GTG | 1248 |
| Trp | Met | Asn | Leu | Ala | Glu | Lys | Ile | Pro | Gln | Ser | Gln | Tyr | Asp | Val | Val | |
| | | | | 405 | | | | | 410 | | | | | 415 | | |
| AGT | GAT | CAT | GTT | AGC | AAA | GTT | ACT | TTT | TTC | AAT | CTG | AAT | GAA | ACC | AAA | 1296 |
| Ser | Asp | His | Val | Ser | Lys | Val | Thr | Phe | Phe | Asn | Leu | Asn | Glu | Thr | Lys | |
| | | | 420 | | | | | 425 | | | | | 430 | | | |
| CCT | CGA | GGA | AAG | TTT | ACC | TAT | GAT | GCA | GTG | TAC | TGC | TGC | AAT | GAA | CAT | 1344 |
| Pro | Arg | Gly | Lys | Phe | Thr | Tyr | Asp | Ala | Val | Tyr | Cys | Cys | Asn | Glu | His | |
| | | 435 | | | | | 440 | | | | | 445 | | | | |
| GAA | TGC | CAT | CAT | CGC | TAT | GCT | GAA | TTA | TAT | GTG | ATT | GAT | GTC | AAT | ATC | 1392 |
| Glu | Cys | His | His | Arg | Tyr | Ala | Glu | Leu | Tyr | Val | Ile | Asp | Val | Asn | Ile | |
| | 450 | | | | | 455 | | | | | 460 | | | | | |
| AAT | ATC | TCA | TGT | GAA | ACT | GAT | GGG | TAC | TTA | ACT | AAA | ATG | ACT | TGC | AGA | 1440 |
| Asn | Ile | Ser | Cys | Glu | Thr | Asp | Gly | Tyr | Leu | Thr | Lys | Met | Thr | Cys | Arg | |
| 465 | | | | | 470 | | | | | 475 | | | | | 480 | |
| TGG | TCA | ACC | AGT | ACA | ATC | CAG | TCA | CTT | GCG | GAA | AGC | ACT | TTG | CAA | TTG | 1488 |
| Trp | Ser | Thr | Ser | Thr | Ile | Gln | Ser | Leu | Ala | Glu | Ser | Thr | Leu | Gln | Leu | |
| | | | | 485 | | | | | 490 | | | | | 495 | | |
| AGG | TAT | CAT | AGG | AGC | AGC | CTT | TAC | TGT | TCT | GAT | ATT | CCA | TCT | ATT | CAT | 1536 |
| Arg | Tyr | His | Arg | Ser | Ser | Leu | Tyr | Cys | Ser | Asp | Ile | Pro | Ser | Ile | His | |
| | | | 500 | | | | | 505 | | | | | 510 | | | |
| CCC | ATA | TCT | GAG | CCC | AAA | GAT | TGC | TAT | TTG | CAG | AGT | GAT | GGT | TTT | TAT | 1584 |
| Pro | Ile | Ser | Glu | Pro | Lys | Asp | Cys | Tyr | Leu | Gln | Ser | Asp | Gly | Phe | Tyr | |
| | | 515 | | | | | 520 | | | | | 525 | | | | |
| GAA | TGC | ATT | TTC | CAG | CCA | ATC | TTC | CTA | TTA | TCT | GGC | TAC | ACA | ATG | TGG | 1632 |
| Glu | Cys | Ile | Phe | Gln | Pro | Ile | Phe | Leu | Leu | Ser | Gly | Tyr | Thr | Met | Trp | |
| | 530 | | | | | 535 | | | | | 540 | | | | | |
| ATT | AGG | ATC | AAT | CAC | TCT | CTA | GGT | TCA | CTT | GAC | TCT | CCA | CCA | ACA | TGT | 1680 |
| Ile | Arg | Ile | Asn | His | Ser | Leu | Gly | Ser | Leu | Asp | Ser | Pro | Pro | Thr | Cys | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| GTC | CTT | CCT | GAT | TCT | GTG | GTG | AAG | CCA | CTG | CCT | CCA | TCC | AGT | GTG | AAA | 1728 |
| Val | Leu | Pro | Asp | Ser 565 | Val | Val | Lys | Pro 570 | Leu | Pro | Pro | Ser | Ser 575 | Val | Lys | |
| GCA | GAA | ATT | ACT | ATA | AAC | ATT | GGA | TTA | TTG | AAA | ATA | TCT | TGG | GAA | AAG | 1776 |
| Ala | Glu | Ile | Thr 580 | Ile | Asn | Ile | Gly | Leu 585 | Leu | Lys | Ile | Ser | Trp 590 | Glu | Lys | |
| CCA | GTC | TTT | CCA | GAG | AAT | AAC | CTT | CAA | TTC | CAG | ATT | CGC | TAT | GGT | TTA | 1824 |
| Pro | Val | Phe 595 | Pro | Glu | Asn | Asn | Leu 600 | Gln | Phe | Gln | Ile | Arg 605 | Tyr | Gly | Leu | |
| AGT | GGA | AAA | GAA | GTA | CAA | TGG | AAG | ATG | TAT | GAG | GTT | TAT | GAT | GCA | AAA | 1872 |
| Ser | Gly 610 | Lys | Glu | Val | Gln | Trp 615 | Lys | Met | Tyr | Glu | Val 620 | Tyr | Asp | Ala | Lys | |
| TCA | AAA | TCT | GTC | AGT | CTC | CCA | GTT | CCA | GAC | TTG | TGT | GCA | GTC | TAT | GCT | 1920 |
| Ser 625 | Lys | Ser | Val | Ser | Leu 630 | Pro | Val | Pro | Asp | Leu 635 | Cys | Ala | Val | Tyr | Ala 640 | |
| GTT | CAG | GTG | CGC | TGT | AAG | AGG | CTA | GAT | GGA | CTG | GGA | TAT | TGG | AGT | AAT | 1968 |
| Val | Gln | Val | Arg | Cys 645 | Lys | Arg | Leu | Asp | Gly 650 | Leu | Gly | Tyr | Trp | Ser 655 | Asn | |
| TGG | AGC | AAT | CCA | GCC | TAC | ACA | GTT | GTC | ATG | GAT | ATA | AAA | GTT | CCT | ATG | 2016 |
| Trp | Ser | Asn | Pro 660 | Ala | Tyr | Thr | Val | Val 665 | Met | Asp | Ile | Lys | Val 670 | Pro | Met | |
| AGA | GGA | CCT | GAA | TTT | TGG | AGA | ATA | ATT | AAT | GGA | GAT | ACT | ATG | AAA | AAG | 2064 |
| Arg | Gly | Pro 675 | Glu | Phe | Trp | Arg | Ile 680 | Ile | Asn | Gly | Asp | Thr 685 | Met | Lys | Lys | |
| GAG | AAA | AAT | GTC | ACT | TTA | CTT | TGG | AAG | CCC | CTG | ATG | AAA | AAT | GAC | TCA | 2112 |
| Glu | Lys 690 | Asn | Val | Thr | Leu | Leu 695 | Trp | Lys | Pro | Leu | Met 700 | Lys | Asn | Asp | Ser | |
| TTG | TGC | AGT | GTT | CAG | AGA | TAT | GTG | ATA | AAC | CAT | CAT | ACT | TCC | TGC | AAT | 2160 |
| Leu 705 | Cys | Ser | Val | Gln | Arg 710 | Tyr | Val | Ile | Asn | His 715 | His | Thr | Ser | Cys | Asn 720 | |
| GGA | ACA | TGG | TCA | GAA | GAT | GTG | GGA | AAT | CAC | ACG | AAA | TTC | ACT | TTC | CTG | 2208 |
| Gly | Thr | Trp | Ser | Glu 725 | Asp | Val | Gly | Asn | His 730 | Thr | Lys | Phe | Thr | Phe 735 | Leu | |
| TGG | ACA | GAG | CAA | GCA | CAT | ACT | GTT | ACG | GTT | CTG | GCC | ATC | AAT | TCA | ATT | 2256 |
| Trp | Thr | Glu | Gln 740 | Ala | His | Thr | Val | Thr 745 | Val | Leu | Ala | Ile | Asn 750 | Ser | Ile | |
| GGT | GCT | TCT | GTT | GCA | AAT | TTT | AAT | TTA | ACC | TTT | TCA | TGG | CCT | ATG | AGC | 2304 |
| Gly | Ala | Ser 755 | Val | Ala | Asn | Phe | Asn 760 | Leu | Thr | Phe | Ser | Trp 765 | Pro | Met | Ser | |
| AAA | GTA | AAT | ATC | GTG | CAG | TCA | CTC | AGT | GCT | TAT | CCT | TTA | AAC | AGC | AGT | 2352 |
| Lys | Val 770 | Asn | Ile | Val | Gln | Ser 775 | Leu | Ser | Ala | Tyr | Pro 780 | Leu | Asn | Ser | Ser | |
| TGT | GTG | ATT | GTT | TCC | TGG | ATA | CTA | TCA | CCC | AGT | GAT | TAC | AAG | CTA | ATG | 2400 |
| Cys 785 | Val | Ile | Val | Ser | Trp 790 | Ile | Leu | Ser | Pro | Ser 795 | Asp | Tyr | Lys | Leu | Met 800 | |
| TAT | TTT | ATT | ATT | GAG | TGG | AAA | AAT | CTT | AAT | GAA | GAT | GGT | GAA | ATA | AAA | 2448 |
| Tyr | Phe | Ile | Ile | Glu 805 | Trp | Lys | Asn | Leu | Asn 810 | Glu | Asp | Gly | Glu | Ile 815 | Lys | |
| TGG | CTT | AGA | ATC | TCT | TCA | TCT | GTT | AAG | AAG | TAT | TAT | ATC | CAT | GAT | CAT | 2496 |
| Trp | Leu | Arg | Ile 820 | Ser | Ser | Ser | Val | Lys 825 | Lys | Tyr | Tyr | Ile | His 830 | Asp | His | |
| TTT | ATC | CCC | ATT | GAG | AAG | TAC | CAG | TTC | AGT | CTT | TAC | CCA | ATA | TTT | ATG | 2544 |
| Phe | Ile | Pro 835 | Ile | Glu | Lys | Tyr | Gln 840 | Phe | Ser | Leu | Tyr | Pro 845 | Ile | Phe | Met | |
| GAA | GGA | GTG | GGA | AAA | CCA | AAG | ATA | ATT | AAT | AGT | TTC | ACT | CAA | GAT | GAT | 2592 |
| Glu | Gly 850 | Val | Gly | Lys | Pro | Lys 855 | Ile | Ile | Asn | Ser | Phe 860 | Thr | Gln | Asp | Asp | |
| ATT | GAA | AAA | CAC | CAG | AGT | GAT | GCA | GGT | TTA | TAT | GTA | ATT | GTG | CCA | GTA | 2640 |
| Ile | Glu | Lys | His 865 | Gln | Ser | Asp | Ala | Gly 870 | Leu | Tyr | Val | Ile | Val 875 | Pro | Val 880 | |

| | | | | | | | | | | | | | | | | |
|---|---|---|---|---|---|---|---|---|---|---|---|---|---|---|---|---|
| ATT | ATT | TCC | TCT | TCC | ATC | TTA | TTG | CTT | GGA | ACA | TTA | TTA | ATA | TCA | CAC | 2688 |
| Ile | Ile | Ser | Ser | Ser | Ile | Leu | Leu | Leu | Gly | Thr | Leu | Leu | Ile | Ser | His | |
| | | | | 885 | | | | | 890 | | | | | 895 | | |
| CAA | AGA | ATG | AAA | AAG | CTA | TTT | TGG | GAA | GAT | GTT | CCG | AAC | CCC | AAG | AAT | 2736 |
| Gln | Arg | Met | Lys | Lys | Leu | Phe | Trp | Glu | Asp | Val | Pro | Asn | Pro | Lys | Asn | |
| | | | 900 | | | | | 905 | | | | | 910 | | | |
| TGT | TCC | TGG | GCA | CAA | GGA | CTT | AAT | TTT | CAG | AAG | ATG | CTT | GAA | GGC | AGC | 2784 |
| Cys | Ser | Trp | Ala | Gln | Gly | Leu | Asn | Phe | Gln | Lys | Met | Leu | Glu | Gly | Ser | |
| | | 915 | | | | | 920 | | | | | 925 | | | | |
| ATG | TTC | GTT | AAG | AGT | CAT | CAC | CAC | TCC | CTA | ATC | TCA | AGT | ACC | CAG | GGA | 2832 |
| Met | Phe | Val | Lys | Ser | His | His | His | Ser | Leu | Ile | Ser | Ser | Thr | Gln | Gly | |
| | 930 | | | | | 935 | | | | | | 940 | | | | |
| CAC | AAA | CAC | TGC | GGA | AGG | CCA | CAG | GGT | CCT | CTG | CAT | AGG | AAA | ACC | AGA | 2880 |
| His | Lys | His | Cys | Gly | Arg | Pro | Gln | Gly | Pro | Leu | His | Arg | Lys | Thr | Arg | |
| 945 | | | | | 950 | | | | | 955 | | | | | 960 | |
| GAC | CTT | TGT | TCA | CTT | GTT | TAT | CTG | CTG | ACC | CTC | CCT | CCA | CTA | TTG | TCC | 2928 |
| Asp | Leu | Cys | Ser | Leu | Val | Tyr | Leu | Leu | Thr | Leu | Pro | Pro | Leu | Leu | Ser | |
| | | | | 965 | | | | | 970 | | | | | 975 | | |
| TAT | GAC | CCT | GCC | AAA | TCC | CCC | TCT | GTG | AGA | AAC | ACC | CAA | GAA | TGA | TCA | 2976 |
| Tyr | Asp | Pro | Ala | Lys | Ser | Pro | Ser | Val | Arg | Asn | Thr | Gln | Glu | * | Ser | |
| | | | 980 | | | | | 985 | | | | | 990 | | | |
| ATA | AAA | AAA | AAA | AAA | | | | | | | | | | | | 2991 |
| Ile | Lys | Lys | Lys | Lys | | | | | | | | | | | | |
| | | | | 995 | | | | | | | | | | | | |

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Ala | Arg | Ala | Thr | Gln | Val | Pro | Glu | Pro | Arg | Pro | Ala | Pro | Ile | Ser | Ala |
| 1 | | | | 5 | | | | | 10 | | | | | 15 | |
| Phe | Gly | Arg | Val | Gly | Pro | Pro | Asp | Gln | Gly | Val | Leu | Leu | | | |
| | | | 20 | | | | | 25 | | | | | | | |

( 2 ) INFORMATION FOR SEQ ID NO:8:

( i ) SEQUENCE CHARACTERISTICS:
        ( A ) LENGTH: 960 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Ser | Lys | Met | Ile | Cys | Gln | Lys | Phe | Cys | Val | Val | Leu | Leu | His | Trp | Glu |
| 1 | | | | 5 | | | | | 10 | | | | | 15 | |
| Phe | Ile | Tyr | Val | Ile | Thr | Ala | Phe | Asn | Leu | Ser | Tyr | Pro | Ile | Thr | Pro |
| | | | 20 | | | | | 25 | | | | | 30 | | |
| Trp | Arg | Phe | Lys | Leu | Ser | Cys | Met | Pro | Pro | Asn | Ser | Thr | Tyr | Asp | Tyr |
| | | 35 | | | | | 40 | | | | | 45 | | | |
| Phe | Leu | Leu | Pro | Ala | Gly | Leu | Ser | Lys | Asn | Thr | Ser | Asn | Ser | Asn | Gly |
| | 50 | | | | | 55 | | | | | 60 | | | | |
| His | Tyr | Glu | Thr | Ala | Val | Glu | Pro | Lys | Phe | Asn | Ser | Ser | Gly | Thr | His |
| 65 | | | | | 70 | | | | | 75 | | | | | 80 |
| Phe | Ser | Asn | Leu | Ser | Lys | Ala | Thr | Phe | His | Cys | Cys | Phe | Arg | Ser | Glu |
| | | | | 85 | | | | | 90 | | | | | 95 | |

```
Gln Asp Arg Asn Cys Ser Leu Cys Ala Asp Asn Ile Glu Gly Arg Thr
            100                 105                 110
Phe Val Ser Thr Val Asn Ser Leu Val Phe Gln Gln Ile Asp Ala Asn
        115                 120                 125
Trp Asn Ile Gln Cys Trp Leu Lys Gly Asp Leu Lys Leu Phe Ile Cys
    130                 135                 140
Tyr Val Glu Ser Leu Phe Lys Asn Leu Phe Arg Asn Tyr Asn Tyr Lys
145                 150                 155                 160
Val His Leu Leu Tyr Val Leu Pro Glu Val Leu Glu Asp Ser Pro Leu
                165                 170                 175
Val Pro Gln Lys Gly Ser Phe Gln Met Val His Cys Asn Cys Ser Val
            180                 185                 190
His Glu Cys Cys Glu Cys Leu Val Pro Val Pro Thr Ala Lys Leu Asn
        195                 200                 205
Asp Thr Leu Leu Met Cys Leu Lys Ile Thr Ser Gly Gly Val Ile Phe
    210                 215                 220
Arg Ser Pro Leu Met Ser Val Gln Pro Ile Asn Met Val Lys Pro Asp
225                 230                 235                 240
Pro Pro Leu Gly Leu His Met Glu Ile Thr Asp Asp Gly Asn Leu Lys
                245                 250                 255
Ile Ser Trp Ser Ser Pro Pro Leu Val Pro Phe Pro Leu Gln Tyr Gln
            260                 265                 270
Val Lys Tyr Ser Glu Asn Ser Thr Thr Val Ile Arg Glu Ala Asp Lys
        275                 280                 285
Ile Val Ser Ala Thr Ser Leu Leu Val Asp Ser Ile Leu Pro Gly Ser
    290                 295                 300
Ser Tyr Glu Val Gln Val Arg Gly Lys Arg Leu Asp Gly Pro Gly Ile
305                 310                 315                 320
Trp Ser Asp Trp Ser Thr Pro Arg Val Phe Thr Thr Gln Asp Val Ile
                325                 330                 335
Tyr Phe Pro Pro Lys Ile Leu Thr Ser Val Gly Ser Asn Val Ser Phe
            340                 345                 350
His Cys Ile Tyr Lys Lys Glu Asn Lys Ile Val Pro Ser Lys Glu Ile
        355                 360                 365
Val Trp Trp Met Asn Leu Ala Glu Lys Ile Pro Gln Ser Gln Tyr Asp
    370                 375                 380
Val Val Ser Asp His Val Ser Lys Val Thr Phe Phe Asn Leu Asn Glu
385                 390                 395                 400
Thr Lys Pro Arg Gly Lys Phe Thr Tyr Asp Ala Val Tyr Cys Cys Asn
                405                 410                 415
Glu His Glu Cys His His Arg Tyr Ala Glu Leu Tyr Val Ile Asp Val
            420                 425                 430
Asn Ile Asn Ile Ser Cys Glu Thr Asp Gly Tyr Leu Thr Lys Met Thr
        435                 440                 445
Cys Arg Trp Ser Thr Ser Thr Ile Gln Ser Leu Ala Glu Ser Thr Leu
    450                 455                 460
Gln Leu Arg Tyr His Arg Ser Ser Leu Tyr Cys Ser Asp Ile Pro Ser
465                 470                 475                 480
Ile His Pro Ile Ser Glu Pro Lys Asp Cys Tyr Leu Gln Ser Asp Gly
                485                 490                 495
Phe Tyr Glu Cys Ile Phe Gln Pro Ile Phe Leu Leu Ser Gly Tyr Thr
            500                 505                 510
Met Trp Ile Arg Ile Asn His Ser Leu Gly Ser Leu Asp Ser Pro Pro
        515                 520                 525
```

-continued

```
Thr Cys Val Leu Pro Asp Ser Val Val Lys Pro Leu Pro Pro Ser Ser
    530                 535                 540
Val Lys Ala Glu Ile Thr Ile Asn Ile Gly Leu Leu Lys Ile Ser Trp
545                 550                 555                 560
Glu Lys Pro Val Phe Pro Glu Asn Asn Leu Gln Phe Gln Ile Arg Tyr
                565                 570                 575
Gly Leu Ser Gly Lys Glu Val Gln Trp Lys Met Tyr Glu Val Tyr Asp
            580                 585                 590
Ala Lys Ser Lys Ser Val Ser Leu Pro Val Pro Asp Leu Cys Ala Val
        595                 600                 605
Tyr Ala Val Gln Val Arg Cys Lys Arg Leu Asp Gly Leu Gly Tyr Trp
    610                 615                 620                 625
Ser Asn Trp Ser Asn Pro Ala Tyr Thr Val Val Met Asp Ile Lys Val
                630                 635                 640
Pro Met Arg Gly Pro Glu Phe Trp Arg Ile Ile Asn Gly Asp Thr Met
                645                 650                 655
Lys Lys Glu Lys Asn Val Thr Leu Leu Trp Lys Pro Leu Met Lys Asn
            660                 665                 670
Asp Ser Leu Cys Ser Val Gln Arg Tyr Val Ile Asn His His Thr Ser
        675                 680                 685
Cys Asn Gly Thr Trp Ser Glu Asp Val Gly Asn His Thr Lys Phe Thr
    690                 695                 700
Phe Leu Trp Thr Glu Gln Ala His Thr Val Thr Val Leu Ala Ile Asn
705                 710                 715                 720
Ser Ile Gly Ala Ser Val Ala Asn Phe Asn Leu Thr Phe Ser Trp Pro
                725                 730                 735
Met Ser Lys Val Asn Ile Val Gln Ser Leu Ser Ala Tyr Pro Leu Asn
            740                 745                 750
Ser Ser Cys Val Ile Val Ser Trp Ile Leu Ser Pro Ser Asp Tyr Lys
        755                 760                 765
Leu Met Tyr Phe Ile Ile Glu Trp Lys Asn Leu Asn Glu Asp Gly Glu
    770                 775                 780
Ile Lys Trp Leu Arg Ile Ser Ser Ser Val Lys Lys Tyr Tyr Ile His
785                 790                 795                 800
Asp His Phe Ile Pro Ile Glu Lys Tyr Gln Phe Ser Leu Tyr Pro Ile
                805                 810                 815
Phe Met Glu Gly Val Gly Lys Pro Lys Ile Ile Asn Ser Phe Thr Gln
            820                 825                 830
Asp Asp Ile Glu Lys His Gln Ser Asp Ala Gly Leu Tyr Val Ile Val
        835                 840                 845
Pro Val Ile Ile Ser Ser Ser Ile Leu Leu Leu Gly Thr Leu Leu Ile
    850                 855                 860
Ser His Gln Arg Met Lys Lys Leu Phe Trp Glu Asp Val Pro Asn Pro
865                 870                 875                 880
Lys Asn Cys Ser Trp Ala Gln Gly Leu Asn Phe Gln Lys Met Leu Glu
                885                 890                 895
Gly Ser Met Phe Val Lys Ser His Ser His Ser Leu Ile Ser Ser Thr
            900                 905                 910
Gln Gly His Lys His Cys Gly Arg Pro Gln Gly Pro Leu His Arg Lys
        915                 920                 925
Thr Arg Asp Leu Cys Ser Leu Val Tyr Leu Leu Thr Leu Pro Pro Leu
    930                 935                 940
Leu Ser Tyr Asp Pro Ala Lys Ser Pro Ser Val Arg Asn Thr Gln Glu
```

(2) INFORMATION FOR SEQ ID NO:9:

(i) SEQUENCE CHARACTERISTICS:
       (A) LENGTH: 6 amino acids
       (B) TYPE: amino acid
       (D) TOPOLOGY: linear (ii) MOLECULE TYPE: protein (xi) SEQUENCE DESCRIPTION: SEQ ID NO:9:

Ser Ile Lys Lys Lys Lys
 1               5

(2) INFORMATION FOR SEQ ID NO:10:

(i) SEQUENCE CHARACTERISTICS:
       (A) LENGTH: 241 base pairs
       (B) TYPE: nucleic acid
       (C) STRANDEDNESS: single
       (D) TOPOLOGY: unknown (ii) MOLECULE TYPE: cDNA (ix) FEATURE:
       (A) NAME/KEY: CDS
       (B) LOCATION: 2..241

(xi) SEQUENCE DESCRIPTION: SEQ ID NO:10:

| A GGA CTT AAT TTT CAG AAG ATG CTT GAA GGC AGC ATG TTC GTT AAG | 46 |
|---|---|
|   Gly Leu Asn Phe Gln Lys Met Leu Glu Gly Ser Met Phe Val Lys | |
|     1               5                  10                 15 | |

| AGT CAT CAC CAC TCC CTA ATC TCA AGT ACC CAG GGA CAC AAA CAC TGC | 94 |
|---|---|
| Ser His His His Ser Leu Ile Ser Ser Thr Gln Gly His Lys His Cys | |
|                     20                 25                 30 | |

| GGA AGG CCA CAG GGT CCT CTG CAT AGG AAA ACC AGA GAC CTT TGT TCA | 142 |
|---|---|
| Gly Arg Pro Gln Gly Pro Leu His Arg Lys Thr Arg Asp Leu Cys Ser | |
|             35                 40                 45 | |

| CTT GTT TAT CTG CTG ACC CTC CCT CCA CTA TTG TCC TAT GAC CCT GCC | 190 |
|---|---|
| Leu Val Tyr Leu Leu Thr Leu Pro Pro Leu Leu Ser Tyr Asp Pro Ala | |
|         50                 55                 60 | |

| AAA TCC CCC TCT GTG AGA AAC ACC CAA GAA TGA TCA ATA AAA AAA AAA | 238 |
|---|---|
| Lys Ser Pro Ser Val Arg Asn Thr Gln Glu *   Ser Ile Lys Lys Lys | |
|     65                 70                      75 | |

| AAA | 241 |
|---|---|
| Lys | |
|  80 | |

(2) INFORMATION FOR SEQ ID NO:11:

(i) SEQUENCE CHARACTERISTICS:
       (A) LENGTH: 73 amino acids
       (B) TYPE: amino acid
       (D) TOPOLOGY: linear (ii) MOLECULE TYPE: protein (xi) SEQUENCE DESCRIPTION: SEQ ID NO:11:

Gly Leu Asn Phe Gln Lys Met Leu Glu Gly Ser Met Phe Val Lys Ser
 1               5                  10                 15

His His His Ser Leu Ile Ser Ser Thr Gln Gly His Lys His Cys Gly
                20                  25                 30

Arg Pro Gln Gly Pro Leu His Arg Lys Thr Arg Asp Leu Cys Ser Leu
            35                  40                 45

Val Tyr Leu Leu Thr Leu Pro Pro Leu Leu Ser Tyr Asp Pro Ala Lys

```
                    5 0                      5 5                      6 0
Ser  Pro  Ser  Val  Arg  Asn  Thr  Gln  Glu
 6 5                      7 0
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Ser  Ile  Lys  Lys  Lys  Lys
                       5
```

( 2 ) INFORMATION FOR SEQ ID NO:13:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: unknown ( i i ) MOLECULE TYPE: cDNA ( i x ) FEATURE:
        ( A ) NAME/KEY: CDS
        ( B ) LOCATION: 2..130

( x i ) SEQUENCE DESCRIPTION: SEQ ID NO:13:

```
A  GGA  CTT  AAT  TTT  CAG  AAG  AAA  ATG  CCT  GGC  ACA  AAG  GAA  CTA  CTG            4 6
   Gly  Leu  Asn  Phe  Gln  Lys  Lys  Met  Pro  Gly  Thr  Lys  Glu  Leu  Leu
    1                  5                           1 0                    1 5

GGT  GGA  GGT  TGG  TTG  ACT  TAG  GAA  ATG  CTT  GTG  AAG  CTA  CGT  CCT  ACC         9 4
Gly  Gly  Gly  Trp  Leu  Thr   *   Glu  Met  Leu  Val  Lys  Leu  Arg  Pro  Thr
                    2 0                           2 5                    3 0

TCG  TGC  GCA  CCT  GCT  CTC  CCT  GAG  GTG  TGC  ACA  ATG                              1 3 0
Ser  Cys  Ala  Pro  Ala  Leu  Pro  Glu  Val  Cys  Thr  Met
               3 5                        4 0
```

( 2 ) INFORMATION FOR SEQ ID NO:14:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gly  Leu  Asn  Phe  Gln  Lys  Lys  Met  Pro  Gly  Thr  Lys  Glu  Leu  Leu  Gly
  1                  5                           1 0                    1 5

Gly  Gly  Trp  Leu  Thr
               2 0
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Glu  Met  Leu  Val  Lys  Leu  Arg  Pro  Thr  Ser  Cys  Ala  Pro  Ala  Leu  Pro
```

```
                         5                           10                          15
Glu Val Cys Thr Met
                20

( 2 ) INFORMATION FOR SEQ ID NO:16:

( i ) SEQUENCE CHARACTERISTICS:
              ( A ) LENGTH: 127 base pairs
              ( B ) TYPE: nucleic acid
              ( C ) STRANDEDNESS: single
              ( D ) TOPOLOGY: unknown ( i i ) MOLECULE TYPE: cDNA ( i x ) FEATURE:
              ( A ) NAME/KEY: CDS
              ( B ) LOCATION: 2..127

( x i ) SEQUENCE DESCRIPTION: SEQ ID NO:16:

A GGA CTT AAT TTT CAG AAG AGA ACG GAC ATT CTT TGA AGT CTA ATC                    46
  Gly Leu Asn Phe Gln Lys Arg Thr Asp Ile Leu  *  Ser Leu Ile
   1               5                  10                  15

ATG ATC ACT ACA GAT GAA CCC AAT GTG CCA ACT TCC CAA CAG TCT ATA                  94
Met Ile Thr Thr Asp Glu Pro Asn Val Pro Thr Ser Gln Gln Ser Ile
                20                  25                  30

GAG TAT TAG AAG ATT TTT ACA TTC TGA AGA AGG                                     127
Glu Tyr  *  Lys Ile Phe Thr Phe  *  Arg Arg
            35                  40

( 2 ) INFORMATION FOR SEQ ID NO:17:

( i ) SEQUENCE CHARACTERISTICS:
              ( A ) LENGTH: 11 amino acids
              ( B ) TYPE: amino acid
              ( D ) TOPOLOGY: linear ( i i ) MOLECULE TYPE: protein ( x i ) SEQUENCE DESCRIPTION: SEQ ID NO:17:

Gly Leu Asn Phe Gln Lys Arg Thr Asp Ile Leu
                 5                  10

( 2 ) INFORMATION FOR SEQ ID NO:18:

( i ) SEQUENCE CHARACTERISTICS:
              ( A ) LENGTH: 21 amino acids
              ( B ) TYPE: amino acid
              ( D ) TOPOLOGY: linear ( i i ) MOLECULE TYPE: protein ( x i ) SEQUENCE DESCRIPTION: SEQ ID NO:18:

Ser Leu Ile Met Ile Thr Thr Asp Glu Pro Asn Val Pro Thr Ser Gln
                 5                  10                  15

Gln Ser Ile Glu Tyr
                20

( 2 ) INFORMATION FOR SEQ ID NO:19:

( i ) SEQUENCE CHARACTERISTICS:
              ( A ) LENGTH: 5 amino acids
              ( B ) TYPE: amino acid
              ( D ) TOPOLOGY: linear ( i i ) MOLECULE TYPE: protein ( x i ) SEQUENCE DESCRIPTION: SEQ ID NO:19:

Lys Ile Phe Thr Phe
```

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:20:

```
Glu Pro Tyr Leu Glu Phe Glu Ala Arg Arg Arg Leu Leu
1               5                   10
```

( 2 ) INFORMATION FOR SEQ ID NO:21:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:21:

```
Glu His Leu Val Gln Tyr Arg Thr Asp Trp Asp His Ser
1               5                   10
```

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:22:

```
Asp His Cys Phe Asn Tyr Glu Leu Lys Ile Tyr Asn Thr
1               5                   10
```

( 2 ) INFORMATION FOR SEQ ID NO:23:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:23:

```
Thr Thr His Ile Arg Tyr Glu Val Asp Val Ser Ala Gly
1               5                   10
```

( 2 ) INFORMATION FOR SEQ ID NO:24:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:24:

```
Pro Phe Pro Leu Gln Tyr Gln Val Lys Tyr Gln Val Lys
```

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:25:

```
Gln Phe Gln Ile Arg Tyr Gly Leu Ser Gly Lys Glu Val
 1               5                  10
```

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:26:

```
Ser Thr Ser Tyr Glu Val Gln Val Arg Val Lys Ala Gln Arg Asn
 1               5                  10                  15
```

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:27:

```
Gln Lys Arg Tyr Thr Phe Arg Val Arg Ser Arg Phe Asn Pro Leu
 1               5                  10                  15
```

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:28:

```
Leu Ser Lys Tyr Asp Val Gln Val Arg Ala Ala Val Ser Ser Met
 1               5                  10                  15
```

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:29:

```
Gly Thr Arg Tyr Thr Phe Ala Val Arg Ala Arg Met Ala Pro Ser
```

(2) INFORMATION FOR SEQ ID NO:30:

(i) SEQUENCE CHARACTERISTICS:
       (A) LENGTH: 15 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:30:

```
Gly Ser Ser Tyr Glu Val Gln Val Arg Gly Lys Arg Leu Asp Gly
 1           5                  10                  15
```

(2) INFORMATION FOR SEQ ID NO:31:

(i) SEQUENCE CHARACTERISTICS:
       (A) LENGTH: 15 amino acids
       (B) TYPE: amino acid
       (C) STRANDEDNESS:
       (D) TOPOLOGY: unknown (ii) MOLECULE TYPE: peptide (xi) SEQUENCE DESCRIPTION: SEQ ID NO:31:

```
Cys Ala Val Tyr Ala Val Gln Val Arg Cys Lys Arg Leu Asp Gly
 1           5                  10                  15
```